United States Patent
Tzipori et al.

(10) Patent No.: US 7,910,096 B2
(45) Date of Patent: *Mar. 22, 2011

(54) HUMAN NEUTRALIZING ANTIBODIES AGAINST HEMOLYTIC UREMIC SYNDROME

(75) Inventors: Saul Tzipori, Shrewsbury, MA (US); Ramaswamy Balakrishnan, Chadds Ford, PA (US); Arthur Donohue-Rolfe, Maynard, MA (US)

(73) Assignee: Trustees of Tufts College, Medford, MA (US)

( * ) Notice: Subject to any disclaimer, the term of this patent is extended or adjusted under 35 U.S.C. 154(b) by 163 days.

This patent is subject to a terminal disclaimer.

(21) Appl. No.: 11/933,166

(22) Filed: Oct. 31, 2007

(65) Prior Publication Data

US 2009/0068176 A1 Mar. 12, 2009

Related U.S. Application Data

(60) Continuation-in-part of application No. 10/041,958, filed on Jan. 7, 2002, which is a continuation-in-part of application No. 09/302,125, filed on Apr. 29, 1999, now abandoned, which is a division of application No. 08/749,704, filed on Nov. 15, 1996, now abandoned.

(51) Int. Cl.
*A61K 39/00* (2006.01)
*A61K 39/395* (2006.01)
*A61K 39/40* (2006.01)

(52) U.S. Cl. ............... 424/130.1; 424/133.1; 424/141.1; 424/142.1; 424/150.1; 424/169.1

(58) Field of Classification Search .................. None
See application file for complete search history.

(56) References Cited

U.S. PATENT DOCUMENTS

| | | | |
|---|---|---|---|
| 4,689,299 A | 8/1987 | Insel et al. | |
| 5,512,282 A | 4/1996 | Krivan et al. | |
| 5,955,293 A | 9/1999 | Keusch et al. | |
| 6,080,400 A | 6/2000 | Williams et al. | |
| 6,255,458 B1 | 7/2001 | Lonberg et al. | |
| 2008/0038262 A1 | 2/2008 | Tzipori et al. | |
| 2008/0107651 A1 | 5/2008 | Tzipori et al. | |

FOREIGN PATENT DOCUMENTS

| | | |
|---|---|---|
| WO | WO 90/07861 | 7/1990 |
| WO | WO 93/18784 A | 9/1993 |
| WO | WO 97/13852 | 4/1997 |
| WO | WO 98/20903 | 5/1998 |
| WO | WO 98/24884 | 6/1998 |
| WO | WO 99/59629 | 11/1999 |

OTHER PUBLICATIONS

37 C.F.R. 1.132 declaration by Dr. Florian Gunzer, dated Apr. 1, 2003.
37 C.F.R. 1.132 declaration by Dr. John. M. Leong, dated Mar. 27, 2003.
37 C.F.R. 1.132 declaration by Dr. Saul Tzipori, dated Apr. 10, 2003.
Akiyoshi, et al., "Characterization of a human monoclonal antibody against Shiga toxin 2 expressed in chinese hamster ovary cells", *Infect.Immun.*, 73:4054-61 (2005).
Baert, et al., "Influence of immunogenicity on the long-term efficacy of infliximab in Crohn's disease", *N. Engl. J. Med.*, 348(7):601-8 (2003).
Banatvala, et al., "The United States National Prospective Hemolytic Uremic Syndrome Study: microbiologic, serologic, clinical, and epidemiologic findings", *J. Infect. Dis.*, 183(7):1063-70 (2001).
Besser, "*Escherichia coli* O157:H7 gastroenteritis and the hemolytic uremic syndrome: an emerging infectious disease", *Annu.Rev.Med.*, 50:355-67 (1999).
Bielaszewska, et al. "Isolation and characterization of sorbitol-fermenting Shiga toxin (verocytotoxin)-producing *Escherichia coli* 0157:H-strains in the Czech Republic", *J. Clin. Microbio.*, 36(7):2135-37 (1998).
Bielaszewska, et al., "Localization of intravenously administered verocytotoxins (Shiga-like toxins) 1 and 2 in rabbits immunized with homologous and heterologous toxoids and toxin subunits", *Infect. Immun.*, 65(7):2509-16 (1997).
Boerlin, et al., "Associations between virulence factors of Shiga toxin-producing *Escherichia coli* and disease in humans", *J. Clin. Microbiol.*, 37:497-503 (1999).
Bonnet, et al., "Non-O157:H7 Stx2-producing *Escherichia coli* strains associated with sporadic cases of hemolytic-uremic syndrome in adults", *J. Clin. Microbiol.*, 36(6):1777-80 (1998).
Bosworth, et al., "Vaccination with genetically modified Shiga-like toxin II prevents edema disease in swine", *Infect. Immun.*, 64:55-60 (1996).
Boyce, et al., "*Escherichia coli* O157:H7 and the hemolytic-uremic syndrome", *N. Engl. J. Med.*, 333(6):364-8 (1995). Boyd, et al., "Alteration of the glycolipid binding specificity of the pig edema toxin from globotetraosyl to globotriaosyl ceramide alters in vivo tissue targetting and results in a verotoxin 1-like disease in pigs", *J. Exp. Med.*, 177:1745-53 (1993).
Brooks, et al., "Non-O157 Shiga toxin-producing *Escherichia coli* infections in the united states, 1983-2002", *J. Infect. Dis.*, 192:1422-1429 (2005).
CDC Drug Service "Diphtheria Antitoxin (Equine)", in *Immunobiologics Distributed by the Centers of Disease Control and Prevention* (2003).
Chalmers, et al., "The surveillance of vero cytotoxin-producing *Escherichia coli* O157 in Wales, 1990 to 1998", *Emerg. Infect. Dis.*, 5(4):566-9 (1999).

(Continued)

*Primary Examiner* — Mark Navarro
(74) *Attorney, Agent, or Firm* — Pabst Patent Group LLP

(57) ABSTRACT

Human and humanized monoclonal antibodies which binds specifically to subunit A of Shiga like toxin II have been developed which are effective to prevent or ameliorate one or more symptoms of HUS in a human. Effective dosages for treatment or prevention range from approximately 0.1 to 5.0 mg of antibody/kg of patient weight. The examples demonstrate the preferred dosage ranges based on the pig model, and what is being tested in phase I clinical trials. Antibodies are preferably transfused over a period of two hours, although this will depend on the patient and the disease state at the time of treatment. Preferred dosages for treatment of humans are between 0.1 mg/kg-5.0 mg/kg of 5C120, or an equivalent dosage of another antibody to subunit A of STX2. In the most preferred embodiments, dosages of 0.1 mg/kg, 0.5 mg/kg, or 5.0 mg/kg of 5C12 (low dose, anticipated therapeutic dose based on animal data and high dose) are administered.

17 Claims, 6 Drawing Sheets

OTHER PUBLICATIONS

Cimolai, "A continuing assessment of risk factors for the development of *Escherichia coli* O157:H7-associated hemolytic uremic syndrome", *Clin. Nephrol.*, 42(2):85-9 (1994).

Cornick, et al., "*Escherichia coli* O157:H7 infections: discordance between filterable fecal shiga toxin and disease outcome", *J. Infect. Dis.*, 186(1):57-63 (2002).

Dean-Nystrom, et al., "*Escherichia coli* O157:H7 causes more-severe systemic disease in suckling piglets than in colostrum-deprived neonatal piglets", *Infect. Immun.*, 68:2356-2358 (2000).

Donohue-Rolfe, et al., "Antibody-based protection of gnotobiotic piglets infected with *Escherichia coli* O157:H7 against systemic complications associated with Shiga toxin 2", *Infect. Immun.*, 67:3645-3648 (1999).

Donohue-Rolfe, et al., "*Escherichia coli* O157:H7 strains that express Shiga toxin (Stx) 2 alone are more neurotropic for gnotobiotic piglets than are isotypes producing only Stx1 or both Stx1 and Stx2", *J. Infect..Dis.*, 181:1825-9 (2000).

Donohue-Rolfe, et al., "Pathogenesis of Shigella diarrhea. IX. Simplified high yield purification of Shigella toxin and characterization of subunit composition and function by the use of subunit-specific monoclonal and polyclonal antibodies", *J. Exp. Med.*, 160(6):1767-81 (1984).

Donohue-Rolfe, et al., "Purification.Of Shiga toxin and Shiga-like toxins I and II by receptor analog affinity chromatography with immobilized p1 glycoprotein and production of cross-reactive monoclonal antibodies", *Infect. Immun.* 57:3888-3893 (1989).

Donohue-Rolfe, et al., "Shiga toxin: purification, structure, and function", *Rev. Infect. Dis.*, 13 Suppl 4:S293-7 (1991).

Downes, et al., "Affinity purification and characterization of Shiga-like toxin II and production of toxin-specific monoclonal antibodies", *Infect. Immun.*, 56:1926-33 (1988).

Edwards, et al., "Vero cell neutralization and mouse protective efficacy of humanized monoclonal antibodies against *Escherichia coli* toxins Stx1 and Stx2", in *Escherichia coli 157:H7 and other Shiga toxin-producing E. coli strains* (Kaper, et al. eds) American Society for Microbiology: Washington D.C., pp. 388-392 (1995).

Engleman, (by Kozbor and Croce), "Fusion partners for human mAbs", in *Human Hybridomas and Monoclonal Antibodies*, (Engleman, et al., eds.), Plenum Press: New York, pp. 23-27 (1985).

Engleman (by Bogard), et al., "Production and characterization of human monoclonal antibodies against gram-negative bacteria", in *Human Hybridomas and Monoclonal Antibodies*, (Engleman, et al., eds.), Plenum Press: New York, pp. 95-112 (1985).

Eklund, et al., "Clinical *Escherichia coli* strains carrying Stx genes: Stx variants and Stx-positive virulence profiles", *J. Clin. Microbiol.*, 40(12):4585-93 (2002).

Francis, "Infection of gnotobiotic pigs with an *Escherichia coli* O157:H7 strain associated with an outbreak of hemorrhagic colitis", *Infect. Immun.*, 51:953-6 (1986).

Friedrich, et al., "*Escherichia coli* harboring Shiga toxin 2 gene variants: frequency and association with clinical symptoms", *J Infect. Dis.*, 185:74-84 (2002).

Fukushima, et al., "Clinical experiences in Sakai City Hospital during the massive outbreak of enterohemorrhagic *Escherichia coli* O157 infections in Sakai City, 1996", *Pediatr. Int.*, 41(2):213-7 (1999).

Gannon, "Characteristics of the Shiga-Like Toxin Produced By *Escherichia coli* Associated With Porcine Edema Disease", *Vet. Microbiol.*, 24:89-100 (1990).

Gannon, "Effects of *Escherichia coli* Shiga-like toxins (verotoxins) in pigs", *Can. J. Vet. Res.*, 53:306-12 (1989).

Garg, et al., "Long-term renal prognosis of diarrhea-associated hemolytic uremic syndrome: a systematic review, meta-analysis, and meta-regression", *JAMA* 290(10):1360-70 (2003).

Goldwater, "Treatment and prevention of enterohemorrhagic *Escherichia coli* infection and hemolytic uremic syndrome", *Expert Rev. Anti. Infect. Ther.*, 5(4):653-63 (2007).

Griffin, "The epidemiology of infections caused by *Escherichia coli* O157:H7, other enterohemorrhagic *E. coli*, and the associated hemolytic uremic syndrome", *Epidemiol. Rev.*, 13:60-98 (1991).

Gunzer, et al., "Gnotobiotic piglets as an animal model for oral infection with O157 and non-O157 serotypes of STEC", *Methods Mol. Med.*, 73:307-27 (2003).

Gunzer, et al., "Gnotobiotic piglets develop thrombotic microangiopathy after oral infection with enterohemorrhagic *Escherichia coli*", *Am. J. Clin. Pathol.*, 118:364-75 (2002).

Gyles, et al., "*Escherichia coli* cytotoxins and enterotoxins", Can J Microbiol., 38(7):734-46 (1992).

Harari, et al., "Carboxy-terminal peptides from the B subunit of Shiga toxin induce a local and parenteral protective effect", *Mol. Immunol.*, 27(7):613-21 (1990).

Hashimoto, et al., "Epidemic of gastrointestinal tract infection including hemorrhagic colitis attributable to Shiga toxin 1-producing *Escherichia coli* O118:H2 at a junior high school in Japan", *Pediatrics*, $103$(1):E2 (1999).

Heffernan, "Human monoclonal antibody (CP101) for the prevention and treatment of HUS and associated complications caused by Shiga toxin *E. coli*.", dated Dec. 2, 2002.

Islam, "Production and characterization of monoclonal antibodies with therapeutic potential against Shiga toxin", *J. Clin. Lab. Immunol.*, 33:11-16 (1990).

Ito, et al., "Cloning and nucleotide sequencing of vero toxin 2 variant genes from *Escherichia coli* o91:h21 isolated from a patient with the hemolytic uremic syndrome", *Microb. Pathog.*, 8:47-60 (1990).

Jackson, et al., "Nucleotide sequence analysis of the structural genes for Shiga-like toxin I encoded by bacteriophage 933j from *Escherichia coli*", *Microb. Pathog.*, 2:147-53 (1987).

Johansen, et al., "Prevention of edema disease in pigs by passive immunization", *Can. J Vet. Res.* 64:9-14 (2000).

Jure, et al., "Association between hemolytic uremic syndrome and verotoxin-producing strains of *E. coli*", *Rev. Latinoam. Microbiol.* 40(1-2):1-8 (1998).

Keusch, et al., "Shiga toxin: production and purification", *Methods Enzymol.*, 165:152-62 (1988).

Khan, et al., "Prevalence and genetic profiling of virulence determinants of non-o157 Shiga toxin-producing *Escherichia coli* isolated from cattle, beef, and humans, Calcutta, India", *Emerg. Infect. Dis.*, 8:54-62 (2002).

Kita, et al., "Pathogenic mechanism of mouse brain damage caused by oral infection with Shiga toxin-producing *Escherichia coli* O157:H7", *Infect. Immun.*, 68(3):1207-14 (2000).

Kitov, et al., "Shiga-like toxins are neutralized by tailored multivalent carbohydrate ligands", *Nature*, 403:669-672 (2000).

Kleanthous, et al., "Haemolytic uraemic syndromes in the British Isles, 1985-8: association with verocytotoxin producing *Escherichia coli*. Part 2: Microbiological aspects", *Arch. Dis. Child.*, 65(7):722-7 (1990).

Klein, et al., "Shiga toxin-producing *Escherichia coli* in children with diarrhea: a prospective point-of-care study", *J. Pediatr.*, 141(2):172-7 (2002).

Levine, "*Escherichia coli* that cause diarrhea: enterotoxigenic, enteropathogenic, enteroinvasive, enterohemorrhagic, and enteroadherent", *J. Infect. Dis.*, 155:377-389 (1987).

Lindgren, "Virulence of enterohemorrhagic *Escherichia coli* o91:h21 clinical isolates in an orally infected mouse model", *Infect. Immun.*,61:3832-3842 (1993).

Lockary, et al., "Shiga toxin-producing *Escherichia coli*, Idaho", *Emerg. Infect. Dis.*, 13(8):1262-4 (2007).

Macconnachie and Todd, "Potential therapeutic agents for the prevention and treatment of haemolytic uraemic syndrome in Shiga toxin producing *Escherichia coli* infection", *Curr. Opin. Infect. Dis.*, 17(5):479-82 (2004).

Macleod, "Reproduction of edema disease of swine with purified Shiga-like toxin-II variant", *Vet. Pathol.*, 28:66-73 (1991).

Macleod, et al., "Immunization of pigs with a purified Shiga-like toxin II variant toxoid", *Vet. Microbiol.*, 29(3-4):309-318 (1991).

Mainil, "Shiga/verocytotoxins and Shiga/verotoxigenic *Escherichia coli* in animals", *Vet. Res.*, 30:235-257 (1999).

Marcato, et al., "Immunoprophylactic potential of cloned Shiga toxin 2 B subunit", *J. Infect. Dis.*, 183(3):435-43 (2001).

Marques, et al., "*Escherichia coli* strains isolated from pigs with edema disease produce a variant of Shiga-like toxin II," *FEMS Microbio. Lett.*, 44(1):33-38 (1987).

Matise, et al., "Intervention with Shiga toxin (Stx) antibody after infection by Stx-producing *Escherichia coli*", J. Infect. Dis., 183(2):347-350 (2001).

Mead and Griffin, "*Escherichia coli* O157:H7", Lancet., 352(9135):1207-12 (1998).

Melton-Celsa, "Activation of Shiga-like toxins by mouse and human intestinal mucus correlates with virulence of enterohemorrhagic *Escherichia coli* O91:H21 isolates in orally infected, Streptomycin-treated mice", Infect. Immun., 64:1569-1576 (1996).

Melton-Celsa, et al., "Virulence of Shiga toxin-producing *Escherichia coli* (stec) in orally-infected mice correlates with the type of toxin produced by the infecting strain", Jpn. J. Med. Sci. Biol., 51 Suppl:S108-S114 (1998).

Milford, et al., "Haemolytic uraemic syndromes in the British Isles 1985-8: association with verocytotoxin producing *Escherichia coli*. Part 1: Clinical and epidemiological aspects", Arch. Dis. Child., 65:716-21 (1990).

Mizuguchi, et al., "Cerebrovascular damage in young rabbits after intravenous administration of Shiga toxin 2", Acta. Neuropathol., 102(4):306-12 (2001).

Moore, et al., "Production of a Shiga-like cytotoxin by *Campylobacter*", Microbial Pathogenesis, 4: 455-462 (1988).

Mukherjee, et al., "Human Stx2-specific monoclonal antibodies prevent systemic complications of *Escherichia coli* O157:H7 infection", Infect. Immun., 70:612-619 (2002).

Mukherjee, et al., "Production and characterization of protective human antibodies against Shiga toxin 1", Infect. Immun., 70:5896-5899 (2002).

Nakao H, et al., "Monoclonal antibody to Shiga toxin 2 which blocks receptor binding and neutralizes cytotoxicity", Infect. Immun., 67:5717-5722 (1999).

Nishikawa, et al., "Relationship of genetic type of Shiga toxin to manifestation of bloody diarrhea due to enterohemorrhagic *Escherichia coli* serogroup O157 Isolates in Osaka City, Japan", J. Clin. Microbiol., 38:2440-2 (2000).

Oi, et al. "Chimeric Antibodies," Biotechniques 4(3): 214-226 (1986).

Ostroff, "Infections with *Escherichia coli* O157:H7 in Washington State. The first year of state wide disease surveillance", JAMA, 262(3):355-359 (1989).

Ostroff, et al. "Toxin genotypes and plasmid profiles as determinants of systemic sequelae in *Escherichia coli* O157:H7 infections", J. Infect. Dis., 160:994-998 (1989).

Padhye, "Production and characterisation of monoclonal antibodies to verotoxins 1 and 2 from *Escherichia coli* of serotype O 157:H7", J. Med. Microbiol., , 30:219-26 (1989).

Paton, "A new biological agent for treatment of Shiga toxigenic *Escherichia coli* infections and dysentery in humans", Nat. Med., 6:265-270 (2000).

Paton, "Polymerase chain reaction amplification, cloning and sequencing of variant *Escherichia coli* Shiga-like toxin type II operons", Microb. Pathog., 15:77-82 (1993).

Paton, et al., "Cloning and nucleotide sequence of a variant Shiga-like toxin II gene from *Escherichia coli* OX3:H21 isolated from a case of sudden infant death syndrome", Microb. Pathog., 13:225-236 (1992).

Paton, et al., "Molecular characterization of a Shiga toxigenic *Escherichia coli* O113:H21 strain lacking eae responsible for a cluster of cases of hemolytic-uremic syndrome", J. Clin. Microbiol., 37(10):3357-61 (1999).

Paton, et al., "Molecular microbiological investigation of an outbreak of hemolytic-uremic syndrome caused by dry fermented sausage contaminated with Shiga-like toxin-producing *Escherichia coli*", J. Clin. Microbiol., 34(7):1622-7 (1996).

Perera, "Isolation and characterization of monoclonal antibodies to Shiga-like toxin II of enterohemorrhagic *Escherichia coli* and use of the monoclonal antibodies in a colony enzyme-linked immunosorbent assay", J. Clin. Microbiol., 26:2127-2131 (1988).

Phillips, et al., "Enterohaemorrhagic *Escherichia coli* O157:H7 target Peyer's Patches in humans and cause attaching/effacing lesions in both human and bovine intestine", Gut, 47:377-81 (2000).

Physician's Desk Reference 34th ed. Charles Baker, Jr., pp. 1140-1141 (1980).

Pierard, et al., "Identification of new verocytotoxin type 2 variant b-subunit genes in human and animal *Escherichia coli* isolates", J. Clin. Microbiol., 36:3317-3322 (1998).

Pradel, et al., "Heterogeneity of Shiga toxin-producing *Escherichia coli* strains isolated from hemolytic-uremic syndrome patients, cattle, and food samples in central France", Appl. Environ. Microbiol., 67(6):2460-8 (2001).

Ramachandran, et al., "The common ovine Shiga toxin 2-containing *Escherichia coli* serotypes and human isolates of the same serotypes possess a Stx2d toxin type", J. Clin. Microbiol., 39(5):1932-7 (2001).

Razzaq, "Hemolytic uremic syndrome: an emerging health risk", Am. Fam. Physician, 74(6):991-6 (2006).

Reisbig, "The cytotoxic activity of shigella toxin. evidence for catalytic inactivation of the 60 s ribosomal subunit", J. Biol. Chem., 256:8739-8744 (1981).

Riley, et al., "Hemorrhagic colitis associated with a rare *Escherichia coli* serotype", N. Engl. J. Med., 308:681-685 (1983).

Russmann, et al., "Variants of Shiga-like toxin II constitute a major toxin component in *Escherichia coli* O157 strains from patients with haemolytic uraemic syndrome", J. Med. Microbiol., 40(5):338-43 (1994).

Russmann, et al., "Genotyping of Shiga-like toxin genes in non-o157 *Escherichia coli* strains associated with Haemolytic Uraemic Syndrome", J. Med. Microbiol., 42:404-410 (1995).

Schmidt, et al., "A new Shiga toxin 2 variant (Stx2f) from *Escherichia coli* isolated from pigeons", Appl. Environ. Microbiol., 66:1205-1208 (2000).

Schmitt, et al., "Two copies of Shiga-like toxin II-related genes common in enterohemorrhagic *Escherichia coli* strains are responsible for the antigenic heterogeneity of the O157:H- strain E32511", Infect. Immun., 59:1065-73 (1991).

Seaner, et al., "Selective effects of *E. coli* Shiga toxin (Stx2) and LPS on macrophages in the kidney of C57/BL/6 mice", Abst. of the Gen. Meet. Am. Soc. Microbio., 120:39 (2002).

Seaner, et al., "Selective effects of *E. coli* Shiga toxin (Stx2) and LPS on neutrophils", Abst of the Gen. Meet. Am. Soc. Microbio., 120:38-39 (2002).

Sheoran, et al., "Human antibody against Shiga toxin 2 administered to piglets after the onset of diarrhea due to *Escherichia coli* O157:H7 prevents fatal systemic complications", Infect. Immun., 73:4607-4613 (2005).

Sheoran, et al., "Stx2-specific human monoclonal antibodies protect mice against lethal infection with *Escherichia coli* expressing Stx2 variants", Infect. Immun., 71:3125-3130 (2003).

Spika, et al., "Hemolytic uremic syndrome and diarrhea associated with *Escherichia coli* O157:H7 in a day care center", J. Pediatr., 109(2):287-91 (1986).

Stephan, et al, "Prevalence and characteristics of verotoxin-producing *Escherichia coli* (VTEC) in stool samples from asymptomatic human carriers working in the meat processing industry in Switzerland", J. Appl. Microbiol., 88(2):335-41 (2000).

Strockbine, et al., "Characterization of monoclonal antibodies against Shiga-like toxin from *Escherichia coli*", Infect. Immun., 50:695-700 (1985).

Takao, et al., "Identity of molecular structure of Shiga-like toxin I (vt1) from *Escherichia coli* O157:H7 with that of Shiga toxin", Microb. Pathog., 5:57-69 (1988).

Takeda, et al., "In vitro assessment of a chemically synthesized Shiga toxin receptor analog attached to Chromosorb P (Synsorb Pk) as a specific absorbing agent of Shiga toxin 1 and 2", Microbiol.Immunol., 43:331-337 (1999).

Tarr, et al., "Genotypic variation in pathogenic *Escherichia coli* O157:H7 isolated from patients in Washington, 1984-1987", J. Infect. Dis., 159(2):344-7 (1989).

Taylor, et al., "A transgenic mouse that expresses a diversity of human sequence heavy and light chain immunoglobulins", Nucl. Acid Res., 20:6287-6295 (1992).

Te Loo, et al., "Binding and transfer of verocytotoxin by polymorphonuclear leukocytes in hemolytic uremic syndrome", Blood, 95:3396-402 (2000).

Te Loo, et al., "Detection of verocytotoxin bound to circulating polymorphonuclear leukocytes of patients with hemolytic uremic syndrome", J. Am. Soc. Nephrol., 12:800-806 (2001).

Te Loo, et al., "Vero cytotoxin binding to polymorphonuclear leukocytes among households with children with hemolytic uremic syndrome", *J. Infect. Dis.*, 184:446-450 (2001).

Tesh, et al., "Comparison of the relative toxicities of Shiga-like toxins type i and type II for mice", *Infect .Immun.*, 61:3392-3402 (1993).

Thomas, et al., "Isolation of Vero cytotoxin-producing *Escherichia coli* serotypes O9ab:H- and O101:H-carrying VT2 variant gene sequences from a patient with haemolytic uraemic syndrome", *Eur. J. Clin. Microbiol. Infect. Dis.*, 13(12):1074-6 (1994).

Trachtman, et al., "Effect of an oral Shiga toxin-binding agent on diarrhea-associated hemolytic uremic syndrome in children: A randomized controlled trial", *JAMA*, 290:1337-1344 (2003).

Tzipori et al. "The role of the eaeA gene in diarrhea and neurological complications in a gnotobiotic piglet model of enterohemorrhagic *Escherichia coli* infection," *Infect. And Immun.*, 63:3621-3627 (1995).

Tzipori, "Cerebral infection with *Escherichia coli* O157:H7 in humans and gnotobiotic piglets", *J. Clin. Pathol.*, 41:1099-1103 (1988).

Tzipori, "Nature and distribution of mucosal lesions associated with enteropathogenic and enterohemorrhagic *Escherichia coli* in piglets and the role of plasmid-mediated factors", *Infect. Immun.*, 57:1142-1150 (1989).

Tzipori, et al., "Antibody therapy in the management of Shiga toxin-induced hemolytic uremic syndrome", *Clin. Microbiol Rev.*, 17(4):926-41 (2004).

Tzipori, et al., "Role of a 60-megadalton plasmid and Shiga-like toxins in the pathogenesis of infection caused by enterohemorrhagic *Escherichia coli* O157:H7 in gnotobiotic piglets", *Infect. Immun.*, 55:3117-3125 (1987).

Van De Kar, et al., "Verocytotoxin-producing *Escherichia coli* infection in hemolytic uremic syndrome in part of western Europe", *Eur. J. Pediatr.*, 155(7):592-5 (1996).

Waddell, "Induction of verotoxin sensitivity in receptor-deficient cell lines using the receptor glycolipid globotriosylceramide", *Proc. Natl. Acad. Sci. USA*, 87:7898-7901 (1990).

Wadolkowski, "Mouse model for colonizatioin and disease caused by enterohemorrhagic *Escherichia coli* O157:H7", *Infect. Immun.*, 58:2438-2445 (1990).

Wadolkowski, et al. "Acute renal tubular necrosis and death of mice orally infected with *Escherichia coli* strains that produce Shiga-like toxin type II", *Infect. Immun.*, 58:3959-3965 (1990).

Watanabe, et al., "Factory outbreak of *Escherichia coli* O157:H7 infection in Japan", *Emerg. Infect. Dis.*, 5(3):424-8 (1999).

Weinstein, et al., "Cloning and sequencing of a Shiga-like toxin type II variant from *Escherichia coli* strain responsible for edema disease of swine", *J. Bacteriol.*, 170(9):4223-30 (1988).

Wong, et al., "The risk of the hemolytic-uremic syndrome after antibiotic treatment of *Escherichia coli* O157:H7 infections", *N. Engl. J. Med.*, 342:1930-1936 (2000).

Wood, et al., "Shiga toxin-specific modulation of platelet activity", *Abst. of the Gen. Meet. Am. Soc. Microbio.*, 120:39 (2002).

Yamagami, et al., "Efficacy of postinfection treatment with anti-Shiga toxin (Stx) 2 humanized monoclonal antibody tma-15 in mice lethally challenged with Stx-producing *Escherichia coli*", *J. Infect. Dis.*, 184:738-742 (2001).

Zhao, et al., "Shiga-like toxin II derived from *Escherichia coli* O157:H7 modifies renal handling of levofloxacin in rats", *Antimicrob. Agents Chemother.*, 46(5):1522-8 (2002).

Zhu, et al., "Identification of Shiga-like toxin *Escherichia coli* isolated from children with diarrhea by polymerase chain reaction", *Chin. Med. J. (Engl).* 115(6):815-8 (2002).

SUMMARY OF Stx2 Hu mAb ACTIVITY
AGAINST CLINICAL Stx2 AND Stx2 VARIANTS

- ● STX 2
- ▲ STX 2a
- ⊠ STX2+STX2a
- ▽ STX 2b
- ○ STX 2c

FIG. 1

HUMAN NEUTRALIZING ANTIBODIES AGAINST HEMOLYTIC UREMIC SYNDROME

CROSS-REFERENCE TO RELATED APPLICATIONS

This application is a continuation-in-part of U.S. Ser. No. 10/041,958, filed Jan. 7, 2002, which is a continuation-in-part of U.S. Ser. No. 09/302,125, filed Apr. 29, 1999, which is a division of U.S. Ser. No. 08/749,704, filed Nov. 1, 1996.

GOVERNMENT SUPPORT

The federal government may have certain rights in the invention since funding for the work described herein was provided in part by the NIH grants R01-AI41326 and R01-DK58993.

FIELD OF THE INVENTION

The present invention relates to dosage forms of human monoclonal antibodies capable of neutralizing Shiga or Shiga-like toxins which cause hemolytic uremic syndrome in humans, a process for the preparation of the new human monoclonal antibody dosage forms, and a method of administration thereof to a human to prevent or treat the development of hemolytic uremic syndrome.

BACKGROUND OF THE INVENTION

Since the first documented outbreaks in 1982, infections from enterohemorrhagic *Escherichia coli* (EHEC), now more commonly referred to as Shiga toxin producing *E. coli* (STEC), have been a major public health concern in the United States and in Europe. It is recognized that the Shiga and Shiga like toxins of *Escherichia coli* 0157:H7 and of other Shiga-producing *E. coli* strains are pathogenesis factors. In the United States, an estimated 73,000 cases of *E. coli* 0157:H7 and 37,000 non-0157 cases occur annually. Most of the cases occur in children less than 5 years of age. The risk of developing hemolytic uremic syndrome (HUS) following EHEC infection is 3-26%. Usually 5-10% of patients with overt STEC disease develop HUS. There is strong evidence that all postdiarrheal HUS is caused by STEC. Complications of HUS can involve the renal, gastrointestinal, or neurologic systems (Razzaq, *Amer. Fam. Physician*, 74(6):991-6 (2006)). HUS is recognized as the major cause of kidney failure in infants and children worldwide. About one-third of HUS patients have abnormal kidney function for many years. Approximately 12 of patients with HUS either develop end stage renal disease or die (Garg, et al, *JAMA*, 290:1360-70 (2003). About 8% have other life long complications such as high blood pressure, seizures, blindness and paralysis (Ostroff, et al., *JAMA*, 262(3):355-9 (1989); Ostroff, et al., *J Infect Dis.*, 160(6):994-8 (1989)). A small percentage, 0.1-2%, die. Of those who survive HUS, one study showed that half had persistent kidney disease, and 18% progress to end stage renal failure. A study estimating the financial repercussions of *E. coli* 0157 infections in the United States suggested that annual cost associated with this pathogen is $405 million, with the cost per case varying from $26 for those who do not seek medical care to $6.2 million for a patient with fatal hemolytic uremic syndrome (HUS) (Lockary V M, et al., Emerg Infect Dis [serial on the Internet]. 2007 Aug. http://www.cdc.gov/EID/content/13/8/1262.htm).

As of October 2007, the Center for Disease Control had reported yet another outbreak of *E. coli* O157, spread by contaminated ground beef. Ill persons reside in 8 states [Connecticut (2), Florida (1), Indiana (1), Maine (1), New Jersey (9), New York (13), Ohio (1), and Pennsylvania (12)]. Thirty-three (89%) of 37 patients with a detailed food history consumed ground beef. Seven illnesses have confirmed associations with recalled products because the strain isolated from the person was also isolated from the meat in their home. Among thirty-three ill persons for whom hospitalization status is known, twenty-one (64%) were hospitalized. Two patients developed a type of kidney failure called hemolytic-uremic syndrome (HUS). No deaths have been reported. The ages of patients range from 1 to 77 years; 50% are between 15 and 24 years old (only 14% of the US population is in this age group).

Even as of 2007, there is no available treatment and antibiotics and anti-diarrheals may exacerbate the problem. Over a quarter century after the discovery of verocytotoxin and the first report by Karmali and colleagues of cases of postdiarrheal hemolytic uremic syndrome (HUS) caused by verotoxigenic *Escherichia coli* (VTEC), otherwise known as Shiga-toxigenic *E. coli* (STEC), successful treatment of these infections has remained elusive, reviewed by Goldwater, Expert Rev Anti Infect Ther. 2007 August; 5(4):653-63, and MacConnachie, et al. Curr Opin Infect Dis. 2004 October; 17(5):479-82 Outbreaks of disease have been reported in association with consumption of hamburgers in fast food chains, in nursing homes and in day-care centers. While consumption of contaminated meats, fruits, vegetable and water have led to outbreaks, person to person contact is now recognized as a key mode of transmission (Spika, et al., *J Pediatr.*, 109(2):287-91 (1986)). Although STEC infection occurs mainly in children, adults are also susceptible. Worldwide incidence of STEC infection and HUS appears to be similar to that found in the U.S. Since 1996 STEC infection is notifiable in most states. The disease peaks in the warm months but may occur at any time of the year. Bloody diarrhea usually occurs prior to systemic complications which can be either fatal, due to acute renal failure and serious neurological involvement, or lead to permanent kidney damage. The kidney damage and the neurological symptoms which are caused by one of 2 toxins is known as hemolytic uremic syndrome (HUS). In children there is normally a prodromal period of 4 to 7 days between the bloody diarrhea and development of HUS. During this prodromal period an effective preventative treatment, if one was available, might prevent the development of HUS.

Currently there are three accepted characteristics of all STEC strains. First, they all harbor lysogenic lambdoid phages that encode the Shiga toxins. Prophage induction is likely required for toxin production. Shiga and Shiga-like toxins were previously referred to as verotoxins due to their toxicity to Vero cells. Shiga-like toxins consist of one enzymatically active A subunit and five B subunits that are responsible for cell binding. The toxins are potent protein synthesis inhibitors and are particularly cytotoxic to both HeLa and Vero cells in culture. Based on antigenic relatedness to Shiga toxin, there are two general classes of Shiga-like toxins. Shiga-like toxin I is neutralized by antibody against Shiga toxin, the toxin produced by *Shigella dysenteriae* type I strains. Shiga-like toxin II is defined as toxin which is not neutralized by antibody directed against Shiga toxin. By amino acid sequence comparison, SLT-I and SLT-II are 56% homologous. The two toxins have identical sets of glycolipid receptors and an identical mode of action. All EHEC strains isolated to date have been found to produce either one toxin or both. The toxins exhibit species specific binding and uptake in the gastrointestinal tract and different strains have different pathogenicity within the same species as well as across species. This has made development of effective treatments extremely difficult due to the general unreliability and lack of predictability of animal models for the human disease.

Therefore, it is an object of the invention to provide 1 human monoclonal antibodies with the ability to neutralize Shiga-like toxin II when the monoclonal antibodies are administered to a human, and thereby treat or prevent toxic uremic syndrome.

It is a further object of the invention to provide human monoclonal antibodies having the ability to neutralize Shiga-like toxin II upon administration to a human, which is dose dependent and has relative few if any adverse side effects.

SUMMARY OF THE INVENTION

A therapeutic method to treat or prevent hemolytic uremic syndrome by administering to a human a dosage effective to prevent or treat one or more symptoms of HUS of a therapeutically effective monoclonal antibody which binds specifically to the A subunit of Shiga like toxin II has been developed. The hemolytic uremic syndrome is typically caused by an enterohemorrhagic *Escherichia coli*. The monoclonal antibody can be either a human monoclonal antibody or a chimeric monoclonal antibody. The monoclonal antibody can be an immunoglobulin produced by a hybridoma resulting from the fusion of a mammalian spleen cell that produces the specific antibody and a myeloma cell that can eternalize cell growth. Alternatively the monoclonal antibody can be produced by a trasfectoma resulting from a myeloma transfected with genes encoding antibody production. The species specific properties largely reside in the heavy chain portions. Transgenic mammals can be genetically engineered to produce only human immunoglobulins and can subsequently produce antibodies in response to antigens. Alternatively cells that already produce antibodies that for instance bear murine species specific immunoglobulin heavy chains can be modified through recombinant DNA technology to produce chimeric antibodies that contain heavy human chain regions.

Administration of the antibodies can be accomplished by several means including oral, intradermal, subcutaneous, intravenous or intramuscular. Antibodies may be supplied as a dosage unit for intravenous administration either in solution or lyophilized. The dosage unit may be diluted in a pharmaceutically acceptable solvent such as 0.9% NaCl (normal saline) just prior to the infusion. Effective dosages for treatment or prevention range from approximately 0.1 to 5.0 mg of antibody/kg of patient weight. The examples demonstrate the preferred dosage ranges based on the pig model, and what is being tested in phase I clinical trials. Antibodies are preferably transfused over a period of two hours, although this will depend on the patient and the disease state at the time of treatment. Preferred dosages for treatment of humans are between 0.1 mg/kg-5.0 mg/kg of 5C120, or an equivalent dosage of another antibody to subunit A of STX2. In the most preferred embodiments, dosages of 0.1 mg/kg, 0.5 mg/kg, or 5.0 mg/kg of 5C12 (low dose, anticipated therapeutic dose based on animal data and high dose) are administered. In this preferred embodiment, a single dose of human monoclonal antibody is infused intravenously using an infusion pump over at least 2 hours.

BRIEF DESCRIPTION OF THE DRAWINGS

FIG. 1 is a graph plotting the relative capabilities of the human monoclonal antibodies 2F10, 3E9, 5C12, 5H8, and 6G3 obtained through the use of a transgenic mouse to neutralize the cytotoxicity of each respective Shiga-like Toxin II variants from clinical isolates: STX2, STX2a, STX2b, STX2c, and STX2+Stx2a. Data is reported as log neutralization index.

DETAILED DESCRIPTION OF THE INVENTION

Figure 2:
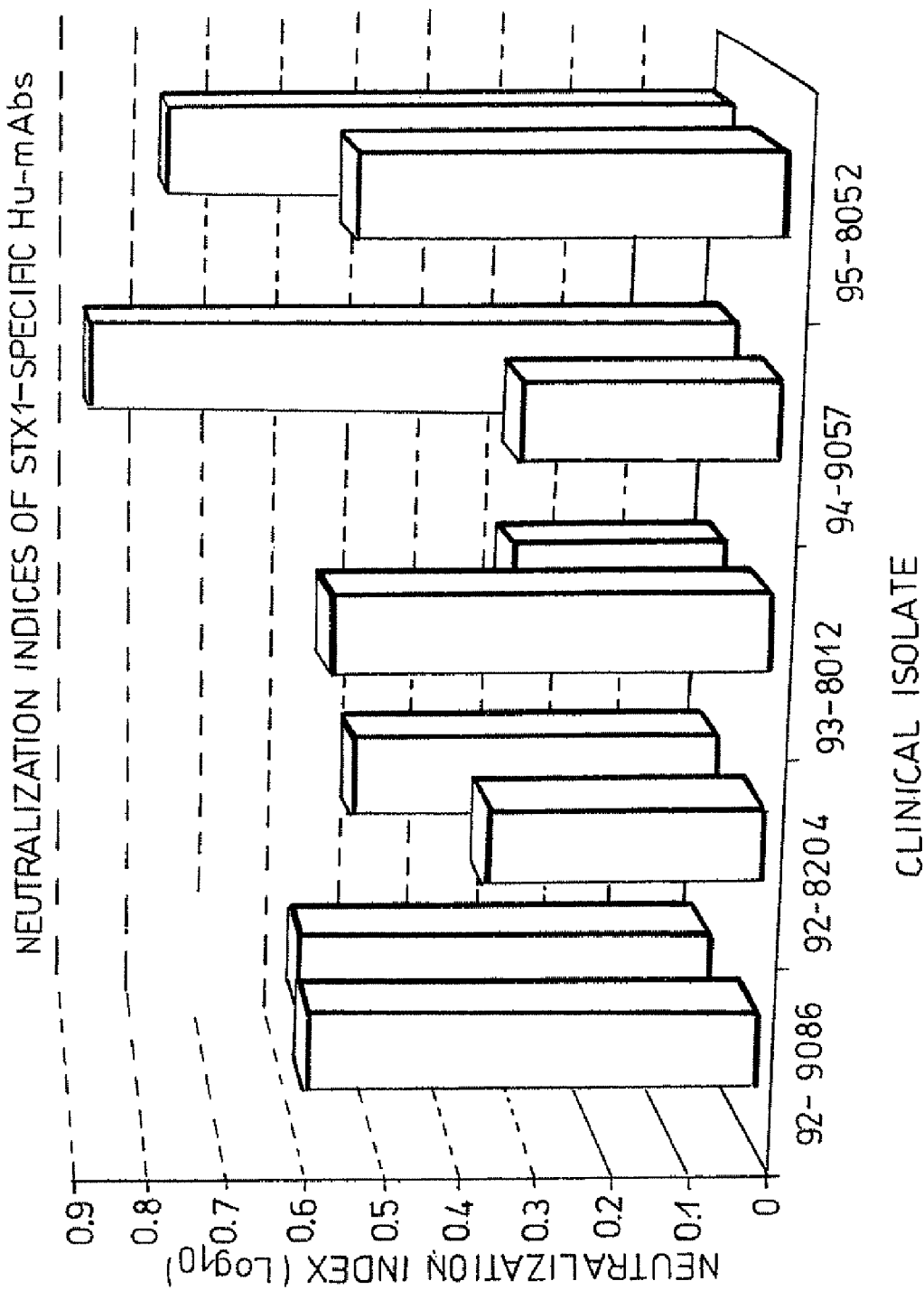
FIG. 2 is a graph showing the relative capabilities of the human monoclonal antibodies 5A4 and 15G2 obtained through the use of a transgenic mouse to neutralize each respective Shiga-like Toxin I obtained from the Stx1 clinical isolates from STEC strains 92-9086, 92-8204, 93-8012, 94-9057, and 95-9052. Data is reported as log neutralization index.
Figure 3:
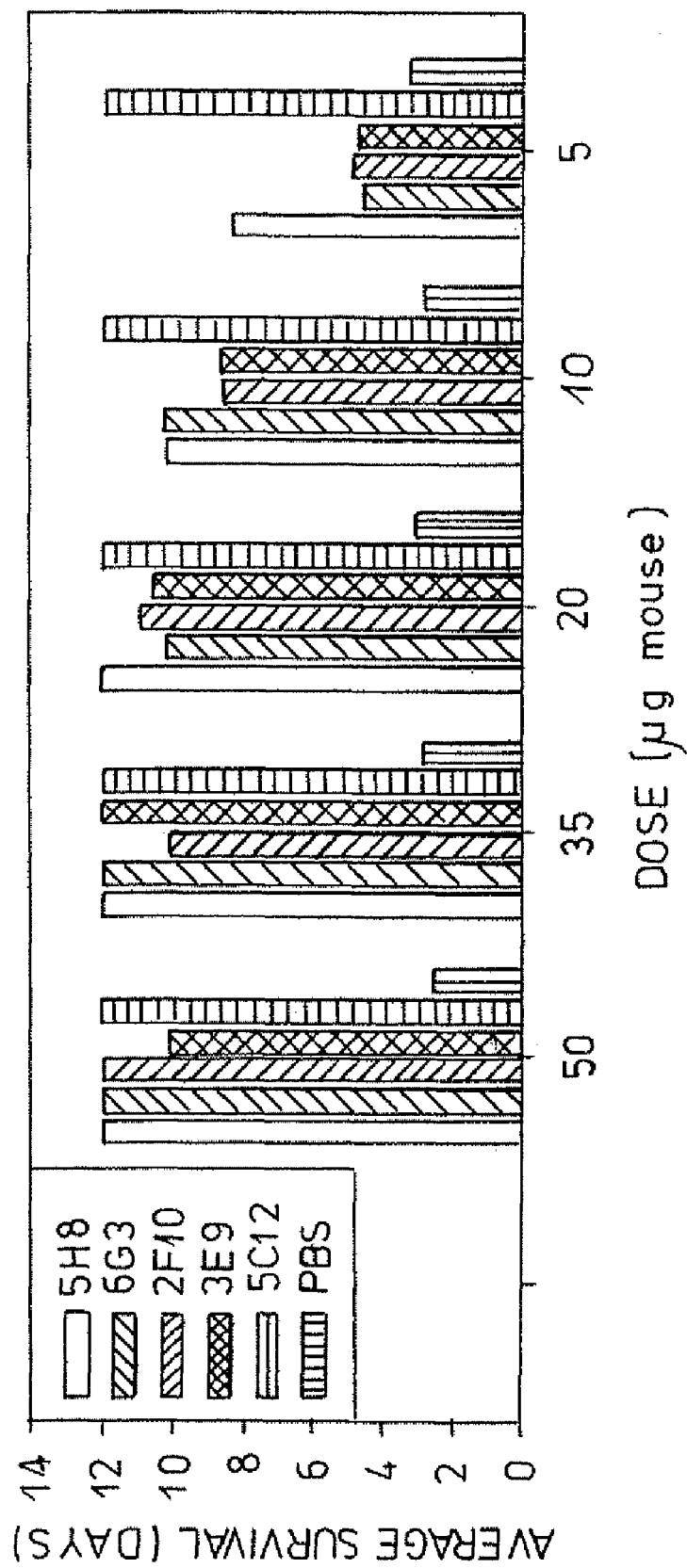
FIG. 3 is a graph comparing the average survival times (days) for mice given 5, 10, 20, 35, or 50 µg of Stx2-specific Hu-mAbs followed 18 hours later with 25 ng Stx2.
Figure 4:
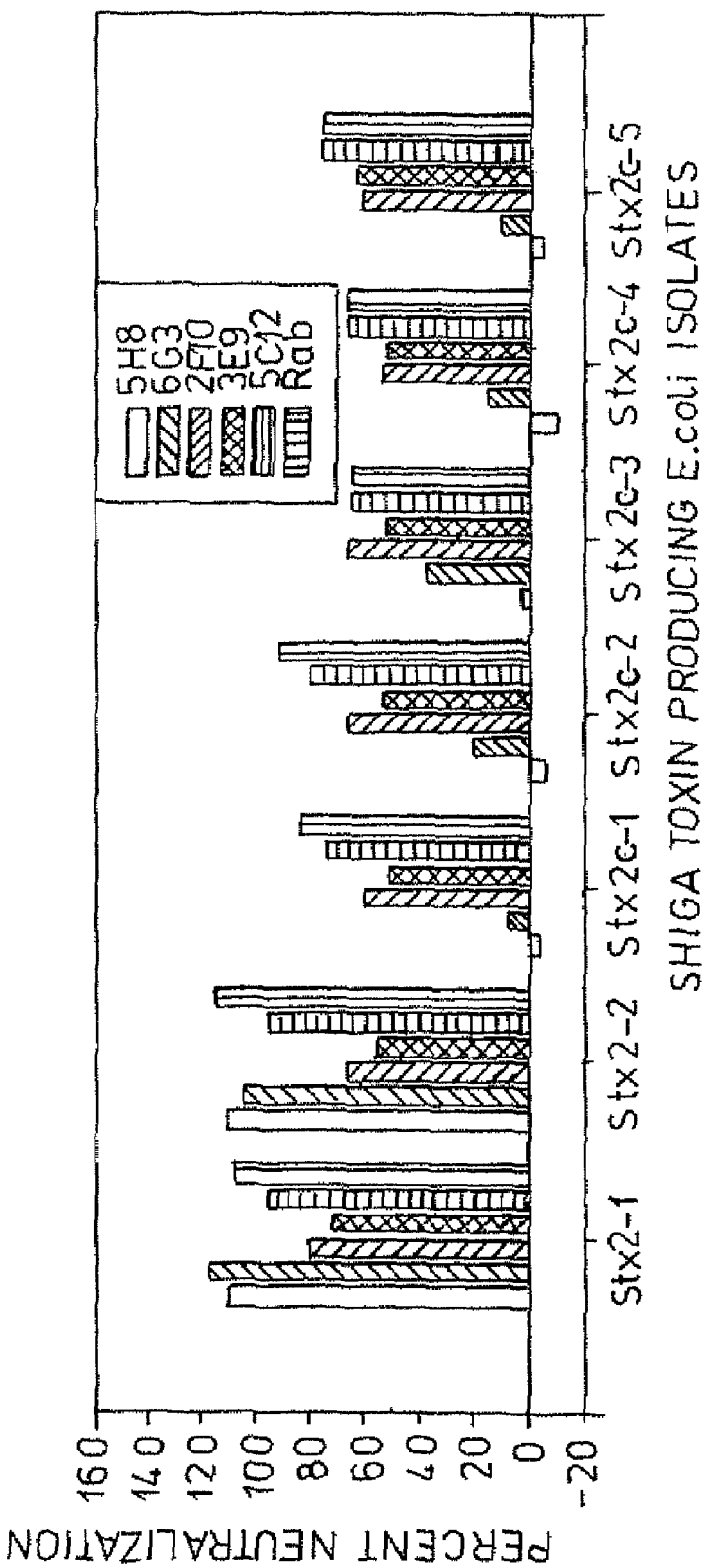
FIG. 4 is a graph comparing the percent in vitro neutralization of Stx2 and Stx2c produced by clinical STEC isolates by Stx2-specific human monoclonal antibodies 5H8, 6G3, 2F10, 3E9 or 5C12, or control rabbit polyclonal antibody.

A therapeutic method to treat-an-individual suffering from or at risk of developing hemolytic uremic syndrome (HUS) caused by a virulent strain of an enterohemorraghic *E. coli* (EHEC) or Shiga toxin producing *E. coli* (STEC) has been developed. Monoclonal antibody, a cocktail of monoclonal antibodies or monospecific polyclonal antibodies, which specifically bind Shiga like toxin II (SLT-II), most preferably the A subunit, are administered in an effective amount to prevent, ameliorate or treat one or more symptoms of infection, most importantly those leading to kidney failure.

Shiga toxin and Shiga like toxin (SLT) are composed of two unique chains, one A subunit and five B subunits, each encoded by toxin genes carried by bacteriophages. The A subunit contains the enzymatic activity, while the five B subunits are responsible for cell binding, HUS is one clinical manifestation among several associated with SLT toxemia and is primarily found to afflict children and the elderly. It has been discovered that it is the A subunit that is most critical to mortality and kidney damage in a person exposed to the toxin, while the B subunit is more closely related to the associated bloody diarrhea. The most common strain of STEC found associated with outbreaks of HUS in the United States is *Escherichia coli* (*E. coli*) 0157:H7.

Not all monoclonal or polyclonal antibodies against a named antigen are the same. The affinity residing in the antigen binding or Fab portions of the immunoglobulin can vary. Shiga toxins consist of A and B subunits. Antibodies against Shiga toxins can be active against A, B, or various combinations of the A and B subunits. These different antibodies do not necessarily have the same affinities, and thus the same neutralizing abilities. These different antibodies may not all neutralize all or the same Shiga toxin variants. The antibodies described herein effectively neutralize Shiga toxins that have been shown to cause hemolytic uremic syndrome, including representative Shiga toxin variants.

The use of antibodies to protect an individual from SLT-II induced disease is described in more detail in the following section. The examples demonstrate, for example, that antibodies with specificity for the A subunit of SLT-II could be used to protect a human from cerebral hemorrhage and mortality following challenge with a virulent SLT-II producing bacterial strain. Although the bulk of the in vivo data reported herein were generated in experiments employing piglet indicator assays for protection against SLT-II, the fundamental principles are applicable to humans as well. The monoclonal and polyclonal antibodies provided herein, which bind to the A subunit of SLT-II, are designed to protect a human individual against the pathologic effects of SLT-II produced by an EHEC, including HUS. Finally, based on the present disclosure, those of skill in the art will recognize that only routine experimentation will be necessary in order to permit them to rapidly identify monoclonal and polyclonal antibodies for application to the therapeutic treatment of human disease.

I. Methods of Administration for Prevention or Treatment of HUS

Persons with, or at risk of developing, HUS can be treated therapeutically or prophylactically. Passive immunization can be accomplished using a prophylactically effective amount of a monoclonal antibody, a cocktail of monoclonal antibodies or monospecific polyclonal antibodies. Preferably, such passive immunization is generally accomplished prior to the onset or in the very early stages of the disease.

To treat or ameliorate one or more symptoms of HUS, a monoclonal antibody, a cocktail of monoclonal antibodies or a monospecific polyclonal antibodies should be given to the affected individual upon detection of the first indications of SLT toxemia. These initial symptoms include the presence of relatively large quantities of blood in diarrhea and bacterial shedding into the feces. If the treatment of HUS is delayed, the amount of a monoclonal antibody, a cocktail of monoclonal antibodies or monospecific polyclonal antibodies necessary to treat the affected individual will likely be greater than if the treatment regimen had begun early after the first signs of EHEC infection were detected. Treatment may also be warranted if a first individual who has shown no indications of STEC infection is exposed to a second individual who has shown the clinical symptoms associated with an STEC infection. This is especially true in cases where the individual is a child or an elderly person.

The examples show that gnobiotic piglets can be protected from the systemic effect of SLT and death with specific antitoxin neutralizing antibodies, even when given well after the bacterial challenge. In this animal model, the piglets present clinical symptoms approximately 48 hours after challenge, which is a shorter time period than humans. Serum Hu-mAb levels of $\geq 0.5$ µg/ml are normally sufficient for protection. The results are statistically significant and indicate that children could likewise be protected against development of renal failure and other systemic complications, if treated early with neutralizing SLT specific antibodies. This is likely to be at the onset of bloody diarrhea or with confirmed infections with SLIT producing bacteria. The benefit of antibody administration earlier to sibling of affected individuals, or in an outbreak in a day-care setting, will be much greater. Systemic administration of SLT antibody however did not protect piglets from developing mucosal lesions of A-E and diarrhea. This study establishes that treatment with highly specific neutralizing antibodies, even when given after exposure, should be beneficial. Since the half-life of exogenous Ig in humans is reported to range between 6 and 14 days, probably a single effective dose might be sufficient.

Studies conducted in the gnobiotic piglet model in which doses of 5C12 ranging from 6.0 mg/kg to 0.05 mg/kg of body weight, administered parenterally 48 h after bacterial challenge, were used to demonstrate that the minimum fully protective antibody dose was 0.4 mg/kg, and the corresponding serum antibody concentration in these piglets was 0.7 µg ($\pm 0.5$)/ml, measured 7 to 14 days after administration. This study also demonstrates that the administration of the Stx2-specific antibody was protective against fatal systemic complications even when it was administered well after the onset of diarrhea and indicate that children treated with this antibody, even after the onset of bloody diarrhea, should be equally protected against the risk of developing HUS. Administration of the antibodies can be accomplished by several means including oral, intradermal, subcutaneous, intravenous or intramuscular.

Antibodies may be supplied as a dosage unit for intravenous administration either in solution or lyophilized. The dosage unit may be diluted in a pharmaceutically acceptable solvent such as 0.9% NaCl (normal saline) just prior to the infusion. Effective dosages for treatment or prevention range from approximately 0.1 to 5.0 mg of antibody/kg of patient weight. The examples demonstrate the preferred dosage ranges based on the pig model, and what is being tested in phase I clinical trials. Antibodies are preferably transfused over a period of two hours, although this will depend on the patient and the disease state at the time of treatment. Preferred dosages for treatment of humans are between 0.1 mg/kg-5.0 mg/kg of 5C120, or an equivalent dosage of another antibody to subunit A of STX2. In the most preferred embodiments, dosages of 0.1 mg/kg, 0.5 mg/kg, or 5.0 mg/kg of 5C12 (low dose, anticipated therapeutic dose based on animal data and high dose) are administered. In this preferred embodiment, a single dose of human monoclonal antibody is infused intravenously using an infusion pump over at least 2 hours.

II. Pharmaceutical MAb Formulations

Monoclonal antibodies which specifically bind the A subunit of SLT-II can be produced by recombinant DNA methodology. Monoclonal antibody fragments (e.g. Fab fragments) can also be produced in this way. One means is through the production of a phage display library and the selection of clones with the appropriate specificity (Monoclonal Antibodies from Combinatorial Libraries, Cold Spring Harbor Course, (1993)). This method involves generation of heavy ($V_H$-$C_{H1}$) and light ($V_L$-$C_L$) chain genes in vitro by methods known to one of skill in the art. The library containing recombinantly produced monoclonal antibody (Fab) fragments is cloned into an M13 surface display vector or its equivalent and the resulting M13 phages or their equivalents, displaying anti-SLT-II antibody (Fab) fragments on their surface are screened and selected by bio-panning. The affinities of the monoclonal antibody (Fab) fragments selected by bio-panning can be further improved through DNA mutagenesis by conventional techniques. A large scale preparation is made from a purified single phage plaque, with the preparation used to either prepare phagemid DNA or purify the SLT-II monoclonal antibody (Fab) fragments expressed on the surface of the M13 phage.

In a second embodiment of the method of manufacture, recombinant DNA methodology is used to produce chimeric monoclonal antibodies which specifically bind the A subunit of SLT-II. Chimeric monoclonal antibodies are created by excising the heavy ($V_H$) and the light ($V_L$) chain genes from the purified M13 phagemid DNA and cloning them into a human immunoglobulin expression vector. In this vector the human immunoglobulin constant regions are spliced to the 3' end of the monoclonal antibody (Fab) fragment, generating a chimeric monoclonal antibody. The immunoglobulin expression vector containing the chimeric monoclonal antibody is transfected by electroporation into a cell line which is defective in Ig chain production.

Transformed cells containing the expression vector encoding the chimeric monoclonal antibody are isolated by conventional means. These cells are then grown in culture and their antibodies purified. Following testing by the methods described above for human monoclonal and monospecific polyclonal antibodies, the chimeric monoclonal antibodies can be used for the therapeutic treatment of individuals suffering from or at risk of HUS.

Any monoclonal antibodies that specifically binds to the A subunit of SLT-II can be used. Monospecific human or humanized polyclonal antibodies which specifically bind to the A subunit of SLT-II can also be used. As used herein, unless otherwise specified, "antibodies" includes antibodies and antibody fragments retaining specific immunoreactivity with SLT-II, preferably the A subunit, which neutralize the toxin activity in vivo.

Deposit of Human Monoclonal Antibodies

Tufts 5C12 human monoclonal antibody to Shiga toxin was deposited by Tufts University on Dec. 20, 2001 under the terms of the Budapest Treaty on the International Recognition of the Deposit of Microorganisms for the purposes of Patent Procedure with the American Type Culture Collection ("ATCC"), Manassas, Va. 20110-2209, United States, Patent Deposit Designation PTA-3944. The deposited antibody will be maintained for at least 30 years from the date of deposit or five years from the most recent request for a sample, whichever is longer. The deposited antibody will be made available upon written request to the ATCC.

The therapeutic amount of antibody given to an individual suffering from HUS will be determined as that amount deemed effective in treating or ameliorating the disease. Normally, a monoclonal antibody, a cocktail of monoclonal antibodies or monospecific polyclonal antibodies will be administered in a pharmaceutically acceptable or compatible carrier. The examples demonstrate the effective dosage ranges based on animal studies, as well as those dosages that are being tested in human clinical trials. Dosages depend on the affinity and specificity of the antibody. 5C12 is an antibody that is extremely effective and is largely dose independent.

Unit dosages will typically consist of one or more vials of antibody, which may be provided in solution, as a lyophilized powder, frozen, or in other forms for delivery and administration of antibodies which are known to those skilled in the art. Typically, the Food and Drug Administration will identify appropriate dosage forms for use in treating patients. Accordingly, dosage formulations will consist of the antibodies, using dry for resuspension or in solution, having a label (as used herein, "label" refers to a label on the container, box containing the container, bag containing the container, and/or package insert associated with the container) which advises the doctor or other caregiver as to the appropriate dosage to administer to an individual in need thereof. Since there is a large range of sizes, from very small children, the primary victims of this deadly disease, to the elderly, who can be much larger, the dosage unit may depend on whether the formulation is for adult or pediatric use. In the most preferred embodiment, the antibody is provided as a highly concentrated solution, which is metered using a syringe or pump into saline or phosphate buffered saline for administration intravenously to a patient. However, for prophylactic use, the antibody may be administered by injection into tissue, muscle, or under the skin. Other routes are known for administration of antibodies. The formulation may be given as a bolus, as a continuous drip, as a series of administrations, or a combination thereof.

III. Methods of Manufacture

The pharmaceutical compositions are prepared by methods known to one of skill in the art. In general, a monoclonal antibody, a cocktail of monoclonal antibodies or monospecific polyclonal antibodies are admixed with a carrier and other diluents necessary to prepare the pharmaceutical composition, so that it is in a stable and administrable form. Administration of the pharmaceutical composition can be accomplished by several means. These means include intradermal, subcutaneous, intravenous or intramuscular, as well as other routes for administration of antibodies known to those skilled in the art. Selection of a particular balanced salt solution or its equivalents will be well known to one of skill in the art.

Purified SLT-II antigen is used to immunize animals for the production of monoclonal or polyclonal antibodies which bind specifically to the A subunit of SLT-II. Production of purified SLT-II antigen is described in detail in the following section. In general, the method takes advantage of the carbohydrate specificity of the toxin's binding domain. SLT-II binds specifically to the $P_1$-glycoprotein purified from hydatid cyst fluid, By coupling the $P_1$-glycoprotein to Sepharose 4B, a solid phase system for capturing toxin is generated. To purify SLT-II, a bacterial lysate containing SLT-II is applied to a column containing the coupled matrix. Non-specifically and weakly binding material is washed off the column, followed by elution of the SLT-II with a buffer containing, for example, 4.5M $MgCl_2$. This method has resulted in yields of purified SLT-II that exceed 80% of the starting material applied to the column. In addition, the purified SLT-II material has been found to have very high specific activity (cytotoxin activity/mg protein). This scheme is improved over those disclosed in the prior art because it is capable of successfully purifying both SLT-I and SLT-II.

In one aspect, human monoclonal and human monospecific polyclonal antibodies are produced by utilizing transgenic mice that are capable of expressing a diversity of human heavy and light chain immunoglobulins. The transgenic mice contain the heavy and light chain protein coding regions in an unrearranged configuration according to published procedures (Taylor, et al., *Nucl. Acid Res.*, 20:6287-6295 (1992)). To produce human monoclonal or human monospecific polyclonal antibodies with the appropriate specificity, transgenic mice are immunized repeatedly with purified SLTII. Following immunization of the transgenic mice, spleen cells are isolated and fused with myeloma cells, thus creating human monoclonal antibody cell lines. The specific methods used to produce hybridomas and monospecific polyclonal antibodies have been described in great detail in the prior art and would be known to one of skill in the art.

The most common method used to purify antigen specific polygonal antibodies from immune serum is immunoaffinity purification on an antigen column. In this method pure antigen, such as SLT-II, is covalently coupled to a solid support.

The immune polyclonal serum is passed through the column, and bound antibody eluted with either a high pH or low pH buffer as disclosed in Antibodies, A Laboratory Manual. Harlow and Lane, Cold Spring Harbor laboratory, 1988.

To determine the neutralizing activity of the human monoclonal or human monospecific polyclonal antibodies specific to the A subunit of SLT-II, tests can be carried out either in vitro in HeLa cells or in vivo in the piglet model (Tzipori, et al., *Infect. and Immun.*, 63:3621-3627, (1995)). Briefly, gnotobiotic piglets are challenged with *E. coli* 0157: H7. At various intervals after inoculation, the human monoclonal or human monospecific polyclonal antibodies are administered at various concentrations to establish the optimal therapeutic dose required to protect them from developing severe neurological symptoms and death. After extensive quality, safety, reactogenicity, and efficacy studies in vitro and in various animal systems, the human monoclonal or human monospecific polyclonal antibodies are tested in human volunteers. Following this initial testing, the human monoclonal or human monospecific polyclonal antibodies are included in a pharmaceutical composition as described above to treat individuals suffering from HUS.

The present invention will be further understood by reference to the following non-limiting examples.

EXAMPLES

Example 1

Development of a Gnotobiotic Piglet Model of Enterohemorrhagic *Escherichia coli* Infection Materials and Methods:
Toxin Purification and Toxoid Production Hydatid cysts isolated from sheep infected with *Echinococcus granulosus* contain material, identified as a glycoprotein, which has $P_1$ blood group reactivity. The $P_1$ glycoprotein's antigenic determinant was subsequently shown to consist of a trisaccharide, Galα-4Galβ1-4G1cNAc, identical to the nonreducing end of the $P_1$ glycolipid on human erythrocytes. Shiga toxin, SLT-I and -II bind to terminal Galα-4Gal disaccharide of glycolipids and hence, the $P_1$-glycolipid is a receptor for these toxins. The $P_1$ glycoprotein in hydatid cyst fluid interacts directly with Shiga toxin and inhibits Shiga toxin binding and cytotoxicity to tissue culture cells. By covalently coupling the hydatid cyst glycoprotein to Sepharose 4B, a solid phase system for capturing toxin is generated. To purify SLT-I, C600(933J) is grown in low syncase medium in the presence of 200 ng/ml of mitomycin C. Mitomycin C induces the 933J bacteriophage carrying the genes for SLT-I. For the purification of SLT-II strain, C600 (933W) is grown in LB broth in the presence of 200 ng/ml mitomycin C. The toxin from both strains is found predominately in the culture supernatant and the approximate yields are 5 mg/liter for SLT-I and 10 mg/liter for SLT-II. A 70% ammonium sulfate precipitation of the culture supernatant is made and the precipitate dissolved in 10 mM Tris (pH 7.4) and dialyzed against the same buffer. To further purify SLT-I and -II, bacterial lysate is applied to a column containing the coupled matrix. To remove nonspecifically or weakly attached proteins, the column is washed with buffer containing 1 M NaCl and finally toxin is eluted with buffer containing 4.5 M $MgCl_2$. For long term storage the eluted protein is dialyzed extensively against 20 mM ammonium bicarbonate, lyophilized and stored at −70° C. This method results in an increase in specific activity (cytotoxin activity/mg protein) of more than 1000 fold, with yields of toxin greater than 800. In addition to the purification of SLT-I and -II, both the SLT-IIe, the toxin involved in edema disease in pigs and a SLT-II variant from a human isolate have been purified. To immunize either GB or the human monoclonal antibody (HuMAb) mice, toxin will be inactivated by treatment with 4% paraformalaldehyde at 37° C. for two days after which the fixative will be removed by overnight dialysis with PBS. The degree of inactivation will be comparing HeLa cell cytotoxicity of the toxoid to the untreated toxin.

Piglet EHEC Challenge and Protection Model

Twenty-two GB piglets were challenged with a high dose of $10^{10}$ EHEC 0157 to ensure that 100% of animals develop fatal neurological symptoms within 40-72 hours. They were then divided into 5 uneven groups as shown in Table 2. One control group remained untreated, while the second was given 12 hours after bacterial challenge 4 ml/kg IP of serum from normal unimmunized pig. Groups 3-5 were similarly given 4 ml/kg IP of SLT-II specific pig immune serum 6, 12 or 24 hours after challenge, respectively. The SLT-II immune pig serum was collected from a weaned pig which was given 4 consecutive intramuscular injections of affinity-purified SLT-II, and stored in aliquots at −70° C.

Assay of SLT II GB Piglet Immune Sera

Toxin (100 pg/ml) was reincubated for 1 h at room temperature with dilutions of either the pig immune serum or dilutions of mouse ascites fluid containing 4D1 mAb. The pretreated toxin was then added to 96 well tissue culture plates containing HeLa cell monolayers. Each mixture of toxin/antibody concentration was added in triplicate. Following overnight incubation at 37° C. the wells were washed and the remaining cells stained by crystal violet, washed and absorbance read at 595 nm. The medium control is used as the 100% survival level.

Results:
Oral Inoculation of Piglets with *E. coli* o157:H7 Strains

In the present study gnotobiotic piglets were inoculated within 24 hours after cesarean section with approximately $10^{10}$ viable *E. coli* 0157:H7 organisms and were observed for symptoms over 5 days. Infected piglets normally develop symptoms of diarrhea within 2-3 days after challenge which continue for several days and result in wasting. Histologically, the mucosa of the terminal ileum and the large intestine are severely damaged due to bacterial A-E lesions mediated by the eaeA gene. Challenge of GB piglets with *E. coli* 0107: H7 strains 931, 3100-85, and 933, all SLT-I & II producers, normally lead to diarrhea and wasting, and some 25-30% of them go on to develop ED-like neurological symptoms (Table 1). In contrast, challenge with *E. coli* 0157:H7 strains 86-24 (Table 1) and RCH/86, both SLT-II producers, result in higher incidence of neurological symptoms and death, reaching 100% of animals. In particular, strain RCH/86 was isolated from a fatal case of bloody diarrhea, complicated with HUS and profound neurological symptoms. In piglets, diarrhea and neurological symptoms develop more rapidly with strain 86-24 than with 933.

TABLE 1

Summary of clinical and histological observations in piglets inoculated with two EHEC and 2 control strains.

| Group number | E. coli strain | Number of animals | Clinical outcome diarrhea | Neurol/coma/death# | A-E lesions* |
|---|---|---|---|---|---|
| 1 | 86-24 (wild) | 8 | 8 | 8 | + |

TABLE 1-continued

Summary of clinical and histological observations in piglets inoculated with two EHEC and 2 control strains.

| Group number | E. coli strain | Number of animals | Clinical outcome diarrhea | Neurol/coma/death# | A-E lesions* |
|---|---|---|---|---|---|
| 5 | 933 (wild) | 16 | 16 | 5 | + |
| 6 | E. coli HS | 4 | 0 | 0 | − |
| 7 | K12 C600 | 2 | 0 | 0 | − |

Piglets were autopsied within 40 to 72 hours after challenge, with onset of symptoms/death.
*Where (−) indicates no bacterial attaching-effacing (A-E) lesions were observed in any of the animals in this group; (+) indicates extensive lesions were observed in the large intestine and in the terminal ileum in all of them.

The intact gut epithelium forms a formidable barrier which keeps the bulk of SLT in the lumen where it is produced by bacteria in large quantities. Although small amount of SLT-II does get through as is demonstrated clinically in humans and experimentally in piglets, most of it remains in the lumen. A fraction however is taken up and remains bound within the gut mucosa as observed by immunohistochemistry (IHC) in frozen sections. In these sections the amount of mucosa-bound SLT-I is many fold higher than mucosa-bound SLT-II, indicating that SLT-I is "stickier" than SLT-II and could be the reason that it does not readily reach the circulation as does the less sticky SLT-II.

SLT-Specific Murine mAbs

Murine monoclonal antibodies (mAb) were raised against SLT-I and SLT-II. In a first attempt, characterization of 5 mAb cell lines produced against Shiga toxin using immunoprecipitation yielded 3 with the appropriate specificity. One example is 4D3, an IgG mAb specific for the B subunit, which neutralized SLT-I very effectively when preincubated with toxin before addition to the HeLa cells. If toxin was prebound to cells first, the antibody had no significant protective effect. In contrast, the other two mAbs which recognized an epitope on the A subunit, showed less dramatic neutralization when preincubated with toxin before addition to HeLa cells. However, these two mAbs were highly protective when added to cells that were prebound with toxin. All 3 mAbs were IgG1. In a second attempt, mAbs were generated against SLT-II. In this study eight hybridomas were isolated and 4 were characterized. The two B subunit specific mabs strongly neutralized SLT-II cytotoxicity to HeLa cells. One of these mAbs also cross-reacted with the SLT-I B subunit and was able to neutralize SLT-I cytotoxicity. The two A subunit mAbs had no neutralizing activity and failed to react against the toxin in solution, but reacted with coated toxin on ELISA plates. The two A subunit specific mAbs were IgM and the two B subunit specific mAbs were IgG, one being IgG1 and the other IgG2b.

Challenge and Protection of GB Piglets

Subsequent to challenge with SLT-II producing E. coli o157:H7, GB piglets were treated with specific antibodies. Table 2 summarizes the outcome of the challenge-protection experiment, in which 7 of the 8 control animals developed neurological symptoms and died within 72 hours. The animal which did survive, suffered episodes of seizure that lasted several seconds. Of the animals given SLT-II pig immune serum, a total of 3 developed neurological symptoms (1 of 6 from the 12 hour group and 2 of 6 from the 24 hour group). Characteristic discreet hemorrhages in the cerebellum associated with the disease were observed only in the 6 euthanized control piglets. It is not clear why the 3 piglets which developed neurological symptoms despite being given only the immune serum had no such cerebellar lesions. All animals that were challenged had A-E lesions in the colon.

TABLE 2

Survival of GB piglets infected with $10^{10}$ organisms of E. coli 0157:H7 strain 86-24, 24 hours after birth.

| Serum given after challenge | Number of animals | Number of animals survived 72 hours | Hemorrhages in cerebellum | A-E lesions |
|---|---|---|---|---|
| No serum given | 2 | 0 | 2 | 2 |
| 12 hr. (control serum) | 6 | 1# | 6 | 6 |
| 6 hr. (SLT serum) | 2 | 2 | 0 | 2 |
| 12 hr. (SLT serum) | 6 | 5 | 0 | 6 |
| 24 hr. (SLT serum) | 6 | 4 | 0 | 6 |

* SLT-II immune serum was produced in a two-months old pig given 4 consecutive intramuscular injections with affinity-purified SLT-II. The control serum was from unimmunized animal.
One surviving piglet displayed occasional fits but survived.
At 6, 12 or 24 after challenge, piglets were injected intraperitoneally (IP) with either 4 ml/kg of SLT-II pig immune serum, or with control pig serum. They were monitored for survival over 72 hours after challenge.

This experiment shows that piglets can be protected from the systemic effect of SLT and death with specific antitoxin neutralizing antibodies, even when given well after the bacterial challenge. In this animal model, the piglets present clinical symptoms approximately 48 hours after challenge, which is a shorter time period than humans. The results are statistically significant and indicate that children could likewise be protected against development of renal failure and other systemic complications, if treated early with neutralizing SLT specific antibodies. This is likely to be at the onset of bloody diarrhea or with confirmed infections with SLT producing bacteria. The benefit of antibody administration earlier to sibling of affected individuals, or in an outbreak in a day-care setting, will be much greater. Systemic administration of SLT antibody however did not protect piglets from developing mucosal lesions of A-E and diarrhea. This experiment confirms the hypothesis that treatment with highly specific neutralizing antibodies, even when given after exposure, is very likely to be beneficial. Since the half-life of exogenous Ig in humans is reported to range between 6 and 14 days, probably a single effective dose might be sufficient. Using human mAbs however, multiple injections, if need be, should be reasonably safe. This might occur if plasma exchange is applied.

Example 2

Construction of Monoclonal Antibodies by Creation of a Phage Display Library

Anti SLT-I and SLT-IT antibodies were generated by phage surface display technology as follows: In this approach, a library of heavy ($V_H$-$C_{H1}$) and Light ($V_L$-$C_L$) chain genes were generated in vitro. This library was cloned into an M13 surface display vector (pComb3 or its equivalent) and the resulting M13 phages, displaying anti SLT I and SLT II antibodies on their surface, were screened and selected by biopanning.

Materials and Methods:

Enrichment of Lymphocytes Secreting Anti SLT I and Anti SLT II Antibodies

Lymphocytes secreting anti SLT-I and anti SLT-II antibodies are enriched according to Linton, et al. (Linton, et al., *Cell*, 59:1049-1059 (1989)). Purified lymphocytes are incubated for 45 minutes with 60 nM biotin-SLT-I or biotin-SLT-II toxin, washed twice, and then poured onto Petri dishes coated with streptavidin and blocked with bovine serum albumin, incubated for another 60 minutes at 4° C., and then washed extensively. After the last wash, the petridishes are shaken dry and the bound cells are used for the isolation of total RNA.

Preparation of Total RNA

Total RNA is prepared either from purified lymphocytes or from purified and enriched lymphocytes by the modified Chomczynski and Sacchi method (Chomczynski and Sacchi, *Anal. Biochem.*, 162:156-15-9 (1987)). Two mls RNAzol (Biotecx) per 10-100 mgs of cells is added and the total RNA is isolated according to the manufacturers' recommendation. The total RNA is precipitated with isopropanol and washed with 70% ethanol and resuspended in TE buffer made with DEPC treated water.

Synthesis of cDNA and PCR Amplification of Heavy ($V_H$-$C_{H1}$) and Light ($V_L$-$C_L$) Chains Monkey heavy and light chain cDNAs are synthesized according to Barbas and Burton (Barbas and Burton, Monoclonal Antibodies from Combinatorial Libraries Cold Spring Harbor Laboratory Course (1993)). 1 μl (10-30 μg) of total RNA is mixed with 1 μl (60 pmoles) of heavy or light chain 3' primer or oligo dT and 54 of DEPC treated water. The mixture is heated to 70° C. and cooled slowly. 5 μl of 5×RT buffer, 2 μl of 10 mM dNTP mixture, 0.5 μl of RNasin, 0.5 μl (200 units) of MMLV Reverse Transcriptase and 5 μl of DEPC treated water are added to the sample and incubated at 37° C. for 45 minutes. The resulting cDNA is used in further DNA amplifications using 5' and 3' heavy and light chain amplifiers in the standard PCR protocols. The PCR primers used in the amplification of heavy and light chains have the following restriction sites that allow the double stranded PCR product to be cloned into the pComb3 vector:

| | | |
|---|---|---|
| 5' Heavy chain primer: | CTCGAG | XhoI |
| 3' Heavy chain primer: | ACTAGT | SpeI |
| 5' Light chain primer: | GAGCTC | SacI |
| 3' Light chain primer: | TCTAGA | XbaI |

Cloning and Expression of the Synthetic Antibodies (Fab), on the Surface of M 13 Bacteriophage Heavy ($V_H$-$C_{H1}$) and light ($V_n$-$C_L$) chain DNAs are amplified using appropriate PCR primers and the cDNA made from the lymphocytes. The amplified double stranded DNA is electrophoretically purified on agarose gels. The purified DNA band (2-5 μg) is cut with suitable restriction enzymes and ligated in pComb3 vector. The ligation mixture is ethanol precipitated and washed with 70% ethanol and air dried. The pellet is dissolved in 10 μl TE. 1-2 μL is used to electroporate XL-1 Blue cells. Transformants are grown at 37° C., in LB amp. After one hour of growth, helper phage VCSM13 is added ($10^{12}$ pfu) and grown for an additional 2 hours. 50 μg/μl of kanamycin is added and the culture is grown overnight at 37° C. M13 phage is prepared from the culture supernatant by standard procedures and is used in biopanning.

Bio-Panning 96 well ELISA plates are coated with 25 μL of either SLT I or SLT II (0.5-0.1 μg/well) in PBS. The plates are incubated at 4° C. for 12 hours. The coating solution is removed and the plates are washed twice with deionized water. After removing the residual water, the plates are blocked with 3% BSA in PBS for 1 hour at 37° C. After removing the 3% BSA solution, 50 μL of phage suspension (approximately ($10^{12}$ pfu) is added to each well and the plates are incubated at 37° C. for 2 hours. At the end, the phage is removed and plates are washed vigorously with TBS/0.5% (TBST). The bound phages are eluted with elution buffer (0.1 M HCl, pH 2.2, adjusted with glycine). This bio-panning is repeated at least three times, with increasing stringency at the wash step and the bound phages are eluted with elution buffer. A large scale phage preparation is made from a purified single phage plaque and the phagemid DNA is prepared. Heavy ($V_H$-$C_{H1}$) and light ($V_L$-$C_L$) chain gene sequences from this plasmid are analyzed. Subsequently, only the variable regions of the heavy ($V_H$) and the light ($V_L$) chain genes are cloned in a human immunoglobulin expression vector. In this vector, the human immunoglobulin constant regions are spliced at the 3' end of the synthetic monkey variable region, generating a synthetic, monkey-human chimeric antibody gene.

Expression and Purification of Recombinant, Monkey-Human Hybrid Anti SLT I and Anti SLT II Antibodies The immunoglobulin expression vector containing the chimeric antibody gene is transfected into mouse myeloma cell line (ATCC CRL 1580), which is defective in IgG chain, by electroporation. After incubation on ice for 10 minutes, the cells are transferred to 20 mls of culture medium and incubated at 37° C. for 48 hours in a $CO_2$ incubator. Cells are plated in a 96 well microtiter plates at density of $2\times10^4$. Cells from the master wells secreting the most antibody are subjected to limiting dilution and are plated. Antibodies from the culture supernatant are purified and used in animal studies.

Example 3

Preparation of Specific Human Monoclonal Antibodies Against Shiga-like Toxin II Using a Transgenic Mouse and Neutralization of this Toxin Using the Monoclonal Antibodies Materials and Methods:
Isolation of Stx2

Stx2 was isolated, purified, and quantified as described in Donohue-Rolfe, et al., *Infect. Immun.*, 57(12):3888-93 (1989). Briefly, Stx2 was isolated from *E. coli* strain C600 (933W) which bears the 933WJ bacteriophage that encodes Stx2. *E. coli* strain C600 (933W) was grown in Modified Syncase Broth at 37° C. with agitation in the presence of 200 ng/ml mitomycin C. Mitomycin C induces the 933J bacteriophage carrying the genes for Stx2. Stx2 in the culture supernatant was precipitated by the addition of 70% ammonium sulfate. The precipitate was dissolved in 10 mM Tris (pH 7.4) and dialyzed against the same buffer. The dialyzed and dissolved precipitate was applied to a Sepharose 4B affinity column containing $P_1$ glycoprotein isolated from *Echinococcus granuloses* hydatid cysts. The $P_1$ glycoprotein contains an antigenic determinant comprised of the trisaccharide, Galα1-4Galβ1-4GlcNAc, which specifically binds Stx1 and Stx2. The column was washed extensively with 1 M NaCl to remove contaminating proteins. Stx2 is eluted from the column with 4.5 M MgCl$_2$. The eluted Stx2 was then dialyzed extensively against 20 mM ammonium bicarbonate, lyophilized and stored at −80° C.

Preparation of Stx2 Toxoid

Stx2 toxoid was prepared by formalin treatment of purified Stx2, Stx2 was purified from cultures of *E. coli* strain C600 (933W) as described above. Inactivation was confirmed by comparing cytotoxicity of the toxoid versus active Stx2 using HeLa cells.

Hu-MAb™ Mouse

Murine hybridomas producing Stx2-specific Hu-mAbs were generated by fusing spleen cells derived from HuMAb Mouse™ mice which contain transgenes bearing human immunoglobulin loci with a non-productive murine myeloma. Three distinct sets of HuMAb Mouse™ mice containing human heavy chain transgenes designated HC2 (Fishwild, et al, *Nat. Biotechnol,* 14, 845-851 (1996)), HCo7 and HFCo12 and the human light chain transgene, KCo5 were used. The heavy chain transgene constructs HC2, HCo7, and HCo12 are comprised of human immunoglobulin heavy chain variable ($V_H$), diversity (D), and joining ($J_H$) segments along with the $\mu$, $\gamma_1 \pm \gamma_3$ constant (C) region exons, the associated switch regions, the $J_H$ intronic enhancer and the rat 3' heavy chain enhancer. The light chain transgene construct KCo5 is comprised of human immunoglobulin light chain variable ($V_k$), joining ($J_k$), and constant ($C_k$) region segments.

To ultimately obtain mice bearing the unrearranged human heavy and light chain immunoglobulin transgenes and unable to produce endogenous murine antibody, two sets of mice were developed. One set of mice lacked the ability to produce endogenous murine antibody. These mice were developed by disrupting the murine kappa light chain locus by injecting mouse embryonic stem cells with a vector containing the neomycin resistance gene. The neomycin resistance gene was disrupted via homologous recombination and both the murine heavy and kappa light chain immunoglobulin gene loci replaced. The embryonic stem cells carrying these targeted disruptions were injected into blastocysts to produce mice bearing deletions of either but not both murine heavy or light chain immunoglobulin loci. Mice bearing deletion of the murine heavy chain immunoglobulin locus were bred to those bearing deletion of the murine light chain immunoglobulin locus to produce mice lacking both murine heavy and kappa light chain immunoglobulin gene loci. A second set of mice bore the human heavy and light chain immunoglobulin transgenes. These mice were developed by injecting mouse embryo pronuclei with one of the human heavy chain immunoglobulin constructs (HC2, HCo7, or HCo12) and the human light chain immunoglobulin construct KCo5 to obtain founder mice bearing both unrearranged human heavy and light chain immunoglobulin gene loci. By breeding mice bearing deletion of both the murine heavy and light chain immunoglobulin gene loci with the mice bearing the human heavy and light chain immunoglobulin gene loci, HuMAb Mouse™ mice capable of expressing human but not murine antibodies were obtained. In response to immunization, it has been demonstrated that these mice can express 1) antibodies that are entirely comprised of human immunoglobulin structural elements; 2) human antibodies of the IgMκ and IgG1κ±IgG3κ isotypes as a result of class-switching; and 3) human antibodies with evidence of extensive somatic mutation within the human variable regions encoding the expressed antibodies. The ability to express human antibodies which undergo class-switching and somatic mutation in response to a variety of antigens, make these mice a unique means of developing human monoclonal antibodies against a multitude of antigens for a variety of therapeutic applications. HuMAb-Mouse™ mice have only 10-50% of the normal level of B cells and only 20-80% respond to a given antigen with sufficiently high titers to be candidates for fusion to produce monoclonal antibodies, however, this can be overcome by immunizing multiple mice.

Generation of Stx2-Specific Hu-mAbs Using Hu-MAb™ Mice

Anti-Stx2 Hu-mAbs were generated by immunizing HC2, HCo7, or HCo12 mice with 10-50 μg Stx2 toxoid emulsified in Freund's Complete (initial immunization only) or Incomplete (all subsequent immunizations) Adjuvant i.p. at biweekly intervals a minimum of three times. Serum anti-Stx2 titers were determined by ELISA on microtiter plates coated with 1.5 μg/ml Stx2 and developed with horseradish peroxidase (HRP)-labeled goat anti-human IgG. The spleens of mice with titers 1:800 were fused to the non-productive murine myeloma, P3×63-Ag8.653, by standard methods. Supernatants from hypoxanthine-aminopterin-thymidine-selected hybridomas were successively screened by ELISA on microtiter plates coated with 1.5 μg/ml Stx2 and developed with horseradish peroxidase (HRP)-labeled goat anti-human IgG or HRP-labeled goat anti-human kappa. Stable, positive clones were selected by subcloning twice by limiting dilution and finally by soft-agar cloning.

Hu-mAb-containing ascitic fluid was prepared by injecting hybridoma cells into the peritoneal cavity of pristane-primed ICR-SCID mice. Hu-mAb concentrations in ascitic fluid were determined relative to those of isotype-matched concentration standards by enzyme-linked immunosorbent assay (ELISA).

Isotype Analysis of Stx2-Specific Hu-mAbs

The isotype of each Stx2 Hu-mAb was determined by ELISA using alkaline phosphatase-labeled anti-human IgM, IgG1, IgG2, IgG3, IgG4, IgA, kappa or lambda.

Analysis of Binding Specificity of Stx2 Hu-mAbs

Stx binding specificity of each Hu-mAb was determined using a sandwich ELISA using murine Stx1 or Stx2-specific mAbs 4D3 or 3D1 to capture Stx1 or Stx2, respectively. Hybridoma culture supernatants containing individual Hu-mAbs were overlaid and developed with alkaline phosphatase-labeled anti-human kappa.

Subunit-Specificity Analysis of Stx2-Specific Hu-mAbs

The subunit specificity of each Stx2 Hu-mAb was determined by Western blot. Stx2 was cross-linked using the homo-bifunctional cross-linking agent, dimethylpimelimidate to create a mixture containing the A subunit bound to one-five B subunits and B subunit alone. The cross-linked Stx2 was electrophoresed by SDS-PAGE on a 15% acrylamide slab gel. Stx2 Hu-mAbs were incubated in the presence of membrane-bound Stx2. Alkaline phosphatase-labeled anti-Fc reagent specific for the anti-Stx2 mAb present, was added to each lane, i.e. goat anti-mouse IgG1 or goat anti-human IgG or IgM. Identification of specific A-B subunit complexes and B subunit multimers was performed as described previously.

In Vitro Neutralization of Stx2

In vitro cytotoxicity assay were used to evaluate the ability of each mAb to neutralize the toxic effects purified Stx2 exerted against HeLa cells. The proportion of surviving cells following exposure to Stx2+Hu-mAb was determined. Stx2-Hu-mAb mixtures were transferred to HeLa cell monolayers and incubated overnight at 37° C. The relative percent neutralization of Stx2 in the presence of Hu-mAb was determined using a standard curve generated based on the effects of Stx2 alone.

Demonstration of Protective Efficacy In Vivo Two different animal models were used to evaluate the potential efficacy of Stx2-specific Hu-mAbs. A murine toxin neutralization assay was used to assess the relative ability of each Hu-mAb to neutralize the activity of Stx2 in vivo. A gnotobiotic piglet model of *E. coli* O157:H7 was used to assess the ability of selected Hu-Abs to neutralize the activity of Stx2 produced in the gastrointestinal tract during infection and systemically absorbed (a situation which simulates that of human disease).

Using the murine Stx2 neutralization assay, the ability of each Hu-mAb to neutralize the effects of Stx2 in vivo was assessed. Dose-response curves were conducted in groups of five 3-4 week old female Swiss Webster mice to determine the amount of Stx2 required to induce 100% mortality in untreated animals. Hu-mAb efficacy was evaluated by administering 50 µg Stx2 Hu-mAb in 1 ml PBS or 1 ml PBS (control) i.p. to each of 8-10 3-4-week old Swiss Webster mice followed by i.v. administration of 25 ng Stx2, 18 hours later. Mice were observed twice daily for survival.

The gnotobiotic piglet model of *E. coli* O157:H7 infection was used to examine the efficacy of selected passively administered Hu-mAbs in preventing the clinical signs and lesions associated with Stx2 during infection. Colostrum-deprived, gnotobiotic piglets were derived by Cesarean section and maintained in sterile microisolators. Within 24 hours following derivation, piglets were orally infected with about $1 \times 10^{10}$ of the Stx2-producing *E. coli* O157:H7 strain, 86-24. This high inoculum usually induces neurological signs and lesions associated with Stx2 activity in >85% of untreated piglets within 48-96 h post-infection (Donohue-Rolfe, et al, *J. Infect. Dis.*, 181(5):1825-9 (2000)). Six or twelve hours following infection, piglets were treated with 3 mg Hu-mAb or an equal volume of PBS (control) administered i.p. Piglets were monitored several times each day for development of severe diarrhea or CNS signs (paddling, head-pressing, fore- and hindlimb paresis, seizures, opisthotonous, and/or ventrally fixed eye deviation) associated with Stx2 activity. Piglets which developed such signs or which were alive at the termination of the experiment (6-10 d post-infection) were euthanized and brain tissue (cerebral cortex, cerebellum) obtained and formalin-fixed for histopathological examination for presence of lesions (hemorrhage, edema) associated with Stx2 activity; blood was obtained for determination of serum Hu-mAb concentration. Serum Hu-mAb concentrations were determined relative to those of isotype-matched concentration standards by enzyme-linked immunosorbent assay (ELISA).

Activity of Stx2 Hu-mAbs Against Stx Produced by Clinical Isolates

An in vitro cytotoxicity assay was utilized to examine the relative efficacy of the Stx2-specific Hu-mAbs against Stx2 and Stx2 variants produced by a panel of clinical STEC isolates. Five Stx2-specific Hu-mAbs (2F10, 3E9, 5C12, 5H8, and 6G3) were selected for testing. The efficacy of each Stx2-specific Hu-mAb was tested against thirty-two strains of STEC. Seventeen STEC strains produced Stx2 alone; 7 produced Stx2a alone; 4 produced Stx2+Stx2a; one produced Stx2b; one produced Stx2b+Stx2; and 2 produced Stx2c alone.

Culture supernatants containing the respective Stx was prepared from each of these STEC strains. *E. coli* O157:H7 strain 90-2380 which produces Stx2 alone was used as a standard toxin control.

Each assay involved preparing a checkerboard of Stx2-specific Hu-mAb and Stx-containing culture supernatural dilutions. Following incubations, $1.5 \times 10^4$ VERO cells were added to each well. Following 48 h incubation at 37° C., assay was developed and read. The neutralization index was defined as the $\log_{10}$ of the dilution of toxin neutralized by 1.25 µg/ml Hu-mAb.

Results:

Isotype and Subunit Specificity of the Stx2 Hu-mAbs

Thirty-seven stable hybridomas were isolated from transgenic mice bearing the human heavy chain transgenes HC2, HCo7, or HCo12 and the human light chain transgene HCo5. Two of these hybridomas were derived from two mice bearing HC2; 21 were derived from 3 mice bearing HCo7; and 14 were derived from 3 mice bearing HCo12. Thirty-six of the 37 hybridomas isolated secrete IgG1κ Hu-mAbs; one secretes an IgG3κ Hu-mAb (Table 3). As determined by ELISA, each hybridoma secretes Hu-mAb specific for Stx2; no cross-reactivity with Stx1 was observed.

The Stx2 subunit specificity of each Hu-mAb was determined by Western blot analysis. Stx2 is comprised of one A subunit of ~32 kD and 5 B subunits each ~7.8 kD. The A versus B subunit-specificity of the anti-Stx2 Hu-mAbs was determined based on binding to covalently cross-linked Stx2 comprised of a mixture of the A subunit bound to zero-five B subunits and B subunit monomers/multimers. Monoclonal antibodies (mAbs) with specificity for the B subunit bind the B subunit monomers/multimers and the A-B complexes; mAbs with specificity for the A subunit bind the A-B complexes but do not bind B subunit monomers/multimers. The relative intensity of binding is determined not only by whether the particular Stx2 entity is recognized by a mAb but also by the percentage of each complex present within the preparation of cross-linked Stx2. Individual Stx2-specific Hu-mAb binding patterns are shown in FIG. 1; the subunit-specificity of each Stx2-specific Hu-mAb is summarized in Table 3. Consistent with either A or B subunit specificity, all 37 Hu-mAbs clearly bound two A-B complexes which based on approximate molecular weights correspond to complexes of the A subunit and 1 or 2 B subunits (A+1B or A+2B). Four Hu-mAbs (3F6, 4G7, 5H8, 6G3) bound entities corresponding to the B subunit monomer (1B) dimer (2B), and trimer (3B), indicating specificity for the B subunit. Although faint, the pattern of 3F6 and 4G7 binding to the 2B and 3B complexes is similar to that of the B subunit-specific murine mAb, 3D1. Both 5H8 and 6G3 however, exhibit different patterns of binding to the B subunit entities-5H8 only binds the 2B complex; 6G3 binds the 1B, 2B, and 3B complexes. These differential patterns of binding are likely indicative of recognition of different epitopes within the B subunit. The lack of binding to B subunit monomer/multimers by the other 33 Hu-mAbs is indicative of specificity for the A subunit. The binding pattern of the A subunit-specific Hu-mAbs is similar, thus differences in epitope specificity cannot be delineated. Consistent with A subunit-specificity, these 33 Hu-mAbs also bind an entity with a molecular weight corresponding to the A subunit monomer (A). Consistent with B subunit specificity, Hu-mAbs 4G7 and 3F6 do not bind the A subunit monomer. However, unexpectedly, the B subunit-specific Hu-mAbs 5H8 and 6G3 and the murine mAb 3D1 do bind the A subunit monomer. This is potentially due to binding an epitope comprised of both A and B subunit moieties.

In Vitro and In Vivo Neutralization of Stx2

The ability of each Hu-mAb to neutralize the activity of purified Stx2 was studied using both in vitro HeLa cell cytotoxicity assays and an in vivo murine model of Stx2 neutralization (Table 3). Two variations of an in vitro cytotoxicity assay were used to determine the amount of Stx2 neutralized by a given amount of each Hu-mAb. In one assay, Hu-mAb concentration was varied in the presence of a constant amount of Stx2 and the percent of Stx2 neutralized was determined at a single concentration for each Hu-mAb (Table 3). In the second assay, Stx2 concentration was varied in the presence of a constant amount of Hu-mAb and the percent of Stx2 neutralized by each Hu-mAb was determined at a single Stx2 concentration (data not shown). Similar results were obtained with both assays. Using the results of the former in vitro assay, each Hu-mAb was grouped into one of three categories based on relative percent neutralization at a single Hu-mAb and Stx2 quantity (39.1 and 1 ng, respectively) as shown in Table 3. Sixteen Hu-mAbs neutralized ≧90% of the Stx2 present (high); 11 neutralized 70-89% of the Stx2 present (medium); and 10 neutralized <70% of the Stx2 present (low).

A murine neutralization assay was used to assess the ability of each Hu-mAb to neutralize Stx2 in vivo. Approximately 18 hours following i.p. administration of 50 μg Hu-mAb, mice were challenged i.v. with 25 ng Stx2. Eight Hu-mAbs (1G3, 2F10, 3E9, 4H9, 5C12, 5H8, 6C3, 6G3; as indicated in Table 3) significantly prolonged average survival to >10 days (experiments were terminated at day 12), relative to the PBS control groups which had average survival values of 2.85-3.9 days. Average in vivo survival did not necessarily correlate with in vitro percent neutralization. Of the 16 Hu-mAbs with high (>90%) in vitro neutralization values, 7 prolonged survival to >10 days; 5 significantly prolonged survival <10 days; and 4 did not significantly prolong survival. Further, one of the 8 Hu-mAbs which prolonged murine survival >10 days had an average in vitro percent neutralization of 81%. Thus the in vivo murine Stx2 neutralization assay provided a more stringent assessment of the Stx2-neutralizing ability of the Hu-mAbs.

TABLE 3

Summary of the Stx2 Hu-mAb isotype, epitope specificity, in vitro and in vivo Stx2 neutralization[a]

| mAb | Iso-type | Stx2 Subunit Speci-ficity | HeLa Cell Cytotoxicity Assay (% Neutralization of Stx2 ± S.D.)[b] | Murine Survival Average ± S.D. (Days) | p-value |
|---|---|---|---|---|---|
| 1G1 | IgG1 | A | 92.0 ± 7.2 | 3.35 ± 0.412 | 0.0101[e] |
| 1G3 | IgG1 | A | 98.6 ± 1.2 | 10.5 ± 3.16 | 0.001[d] |
| 2F10 | IgG1 | A | 99.6 ± 0.3 | 12.0 ± 0 | 0.001[d] |
| 3E9 | IgG1 | A | 99.2 ± 0.7 | 12.0 ± 0 | 0.001[d] |
| 4G7 | IgG1 | A | 99.3 ± 0.2 | 6.1 ± 4.095 | 0.0035[e] |
| 4H9 | IgG1 | A | 94.5 ± 3.1 | 10.25 ± 3.691 | 0.0018[f] |
| 5A4 | IgG1 | A | 97.7 ± 2.1 | 8.7 ± 4.27 | 0.0011[d] |
| 5C12 | IgG1 | A | 99.7 ± 0.3 | 12.0 ± 0 | 0.001[e] |
| 5H8 | IgG1 | A + B | 96.0 ± 2.2 | 11.2 ± 2.53 | 0.001[d] |
| 6G3 | IgG1 | A + B | 98.4 ± 2.1 | 12.0 ± 0 | 0.001[e] |
| 6H5 | IgG1 | A | 94.7 ± 2.2 | 3.1 ± 0.81 | 0.4680[d] |
| 6H7 | IgG1 | A | 90.4 ± 3.8 | 2.7 ± 0.35 | 0.0071[d] |
| 7C4 | IgG1 | A | 99.5 ± 0.2 | 7.65 ± 4.59 | 0.0156[d] |
| 9F9 | IgG1 | A | 95.7 ± 1.7 | 5.38 ± 4.095 | 0.2190[e] |
| 9H9 | IgG1 | A | 94.3 ± 1.1 | 4.35 ± 4.095 | 0.3737[d] |
| 12C12 | IgG1 | A | 97.9 ± 2.4 | 4.3 ± 2.72 | 0.1579[d] |
| 1C3 | IgG1 | A | 86.2 ± 4.5 | 2.9 ± 0.61 | 0.2380[d] |
| 2G5 | IgG1 | A | 87.2 ± 11.7 | 5.1 ± 3.78 | 0.4047[d] |
| 4H10 | IgG1 | A | 73.7 ± 12.4 | 8.5 ± 4.52 | 0.0012[e] |
| 5A8 | IgG1 | A | 82.2 ± 6.2 | 3.7 ± 2.96 | 0.3495[d] |
| 5B11 | IgG1 | A | 81.3 ± 1.5 | 3.3 ± 0.89 | 0.9004[d] |
| 5E12 | IgG1 | A | 84.2 ± 2.4 | 4.0 ± 2.88 | 0.7591[d] |
| 6C3 | IgG1 | A | 81.3 ± 14.2 | 12.0 ± 0 | 0.001[e] |
| 6D8 | IgG1 | A | 78.7 ± 12.1 | 3.2 ± 0.363 | 0.0254[e] |
| 6E6 | IgG1 | A | 86.7 ± 4.1 | 2.8 ± 0.63 | 0.1989[d] |
| 7G2 | IgG1 | A | 75.0 ± 11.5 | 3.2 ± 0.350 | 1.000[f] |
| 1G12 | IgG1 | A | 46.4 ± 22.0 | 3.1 ± 0.211 | 0.0292[e] |
| 3A2 | IgG1 | A | 47.3 ± 41.5 | 3.85 ± 2.868 | 0.5983[f] |
| 3F6 | IgG1 | B | 22.0 ± 38.1 | 2.8 ± 0.258 | 0.1888[e] |
| 5F2 | IgG1 | A | 62.7 ± 0.6 | 4.15 ± 2.78 | 0.0129[e] |
| 6B7 | IgG1 | A | 60.5 ± 52.6 | 3.45 ± 0.956 | 0.0227[e] |
| 6C12 | IgG1 | A | 51.4 ± 40.6 | 3.7 ± 0.63 | 0.0012[d] |
| 7B3 | IgG1 | A | 69.2 ± 11.1 | 3.1 ± 0.70 | 0.4664[d] |
| 7F2 | IgG1 | A | 64.3 ± 28.1 | 5.95 ± 4.186 | 0.0047[e] |
| 10E9 | IgG1 | A | 62.0 ± 15.1 | 2.75 ± 0.354 | 0.0230[e] |
| 11B12 | IgG1 | A | 52.0 ± 45.0 | 4.15 ± 2.769 | 0.0041[e] |

[a]Hu-mAbs have been sorted into three groups based on average percent neutralization of Stx2 in vitro. Within table, groups are divided using double lines. Upper, middle, and lower groups include Hu-mAbs with in vitro percent neutralization values of ≧90%, 70-89%, and <70%, respectively. Each percent neutralization represents the average of 3 values obtained from independent experiments.
[b]Average percent neutralization of 1 ng Stx2 in presence of 39.1 ng Hu-mAb.
[c]Experiments were terminated on day 12; n = 8-10 mice per group. Hu-mAbs which prolonged survival an average of >10 days are indicated in bold type.
[d]Survival of PBS control was 3.3 ± 0.35 days.
[e]Survival of PBS control was 2.85 ± 0.24 days.
[f]Survival of PBS control was 3.9 ± 2.85 days.

Protection of Gnotobiotic Piglets Infected with E. Coli 0157:H7

Four (2F10, 3E9, 5C12, 5H8) of the eight Hu-mAbs most effective at prolonging murine survival were further studied in a gnotobiotic piglet model of E. coli 0157:H7 infection. In this model, 80% of untreated piglets develop neurological signs (Donohue-Rolfe, et al, J Infectious Diseases, 181(5): 1825-9 (2000)). The gnotobiotic piglet model differs substantially from the murine Stx2 neutralization assay; 1) Instead of receiving purified Stx2, piglets are infected with an Stx2-producing strain of E. coli 0157:H7 and thus develop diarrhea and can become dehydrated similar to humans; and 2) Hu-mAbs are given 6 or 12 h following infection rather than prior to challenge, thereby simulating the situation likely to occur in humans in which Hu-mAbs would be administered following diarrhea development in an effort to prevent HUS. Three parameters were used to assess the effect of Hu-mAb administration relative to untreated PBS control piglets: 1) Prevention of neurological signs (paddling, head-pressing, ataxia, convulsions); 2) Ability to prolong survival; and 3) Prevention of neurological lesions (hemorrhage and edema) within the cerebral cortex and/or cerebellum. Constant monitoring was not possible and as a result piglets occasionally died without the opportunity to observe them during the hours preceding death. For these piglets it is not known whether CNS signs developed and furthermore, examination of brain tissue was not possible. Thus only piglets observed up until the time of death or euthanasia were included in determinations of presence or absence of CNS signs and lesions; however, all piglets which died or were euthanized due to experimental manipulations were included in the survival data. Piglets which died or were euthanized due to unrelated causes (esophageal puncture, extreme weakness, insufficient nourishment and/or severe dehydration) were excluded from the experimental data altogether.

A total of 9 experiments were performed to evaluate the efficacy of administering Hu-mAbs 2F10, 3E9, 5C12, or 5H8, 6 or 12 hours following infection (4 representative experiments are shown in Table 4). Nineteen of 21 (90%) control piglets observed immediately prior to death or euthanasia developed neurological signs and 22 of 23 (96%) available for histologic examination had evidence of neurological lesions. In contrast, administration of Hu-mAbs 2F10, 3E9, 5C12, or 5H8, 6 or 12 hours post-infection prevented development of neurological signs and lesions in 39 of 42 (93%) treated piglets in these 9 experiments. Two treated piglets which did exhibit convincing neurological signs and lesions had serum Hu-mAb levels <0.01 µg/ml in contrast to the levels of 0.488-15.2 µg/ml in piglets which did not develop neurological signs and/or lesions. Interestingly, one piglet which exhibited both neurological signs and lesions and a second piglet which exhibited only mild neurological lesions, had serum Hu-mAb levels of 2.0 and 8.9 µg/ml, respectively. Although dose response studies have not been performed, and these two treated piglets which exhibited lesions±signs had Hu-mAb levels within the range of those which were protected, this data nonetheless suggests serum Hu-mAb levels of $\geq 0.5$ µg/ml are normally sufficient for protection.

In addition to preventing development of fatal CNS signs and lesions, Hu-mAb administration also resulted in a trend toward prolongation of survival. Due to the small sample size present within each experimental group, prolongation of survival of Hu-mAb treated groups versus PBS control groups was not always statistically significant. Nonetheless, the average survival of Hu-mAb groups was greater than control groups in each experiment with the exception of one 3E9 treated group containing a single piglet (data not shown). Significant prolongation of survival was observed at least twice following administration of Hu-mAbs 3E9, 5H8, or 5C12 at 6 or 12 h post-infection. Comparison of all 44 Hu-mAb treated pigs versus all 31 PBS control pigs indicates Hu-mAb administration does indeed prolong survival ($p \leq 0.0001$).

Figure 5:
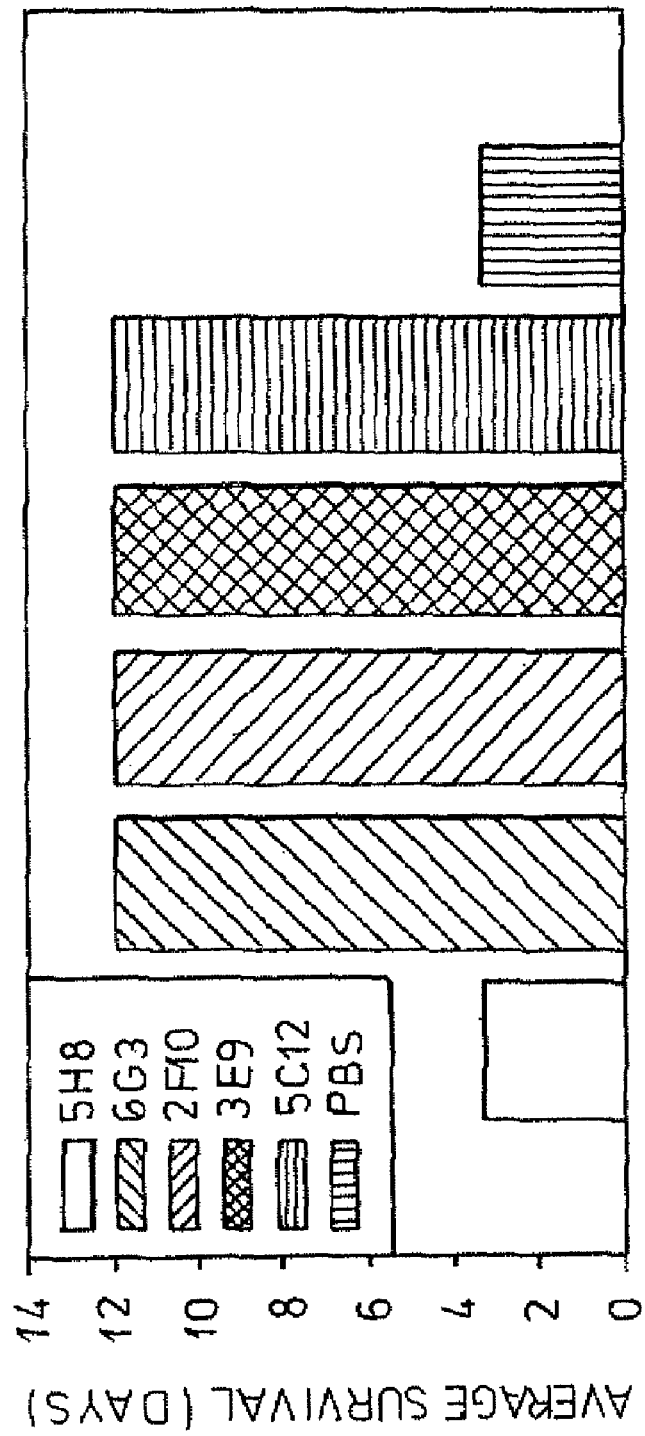
FIG. 5 is a graph comparing the average survival time (days) of mice given 30 µg of Stx2-specific human monoclonal antibodies 5H8, 6G3, 2F10, 3E9 or 5C12 or control PBS followed 18 hours later with 25 ng Stx2c containing culture supernatant obtained from Stx2c producing *E. coli* isolate (95-8061).
Figure 6:
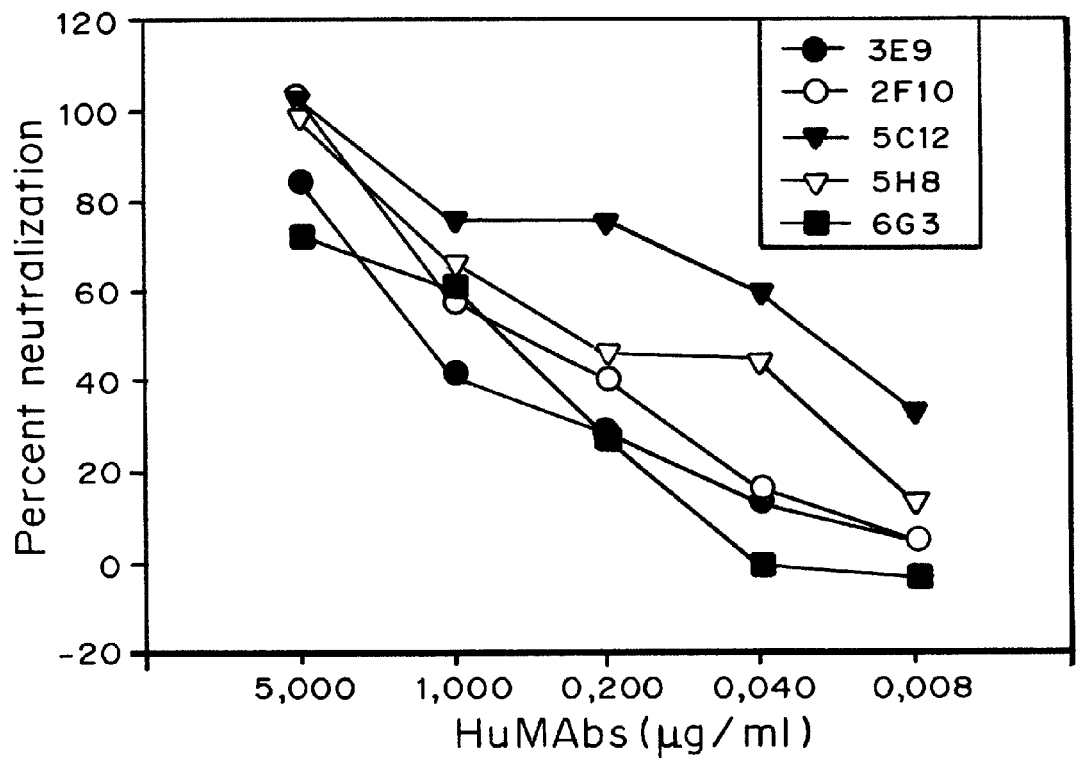
FIG. 6 is a graph showing the percent neutralization of Stx2-mediated HeLa cell cytotoxicity by Stx2-specific HuMAbs as a function of dose in micrograms/ml. All Stx2-specific HuMAbs neutralized Stx2 at the highest concentration of 5 µg/ml and showed dose dependency.
Figure 7:
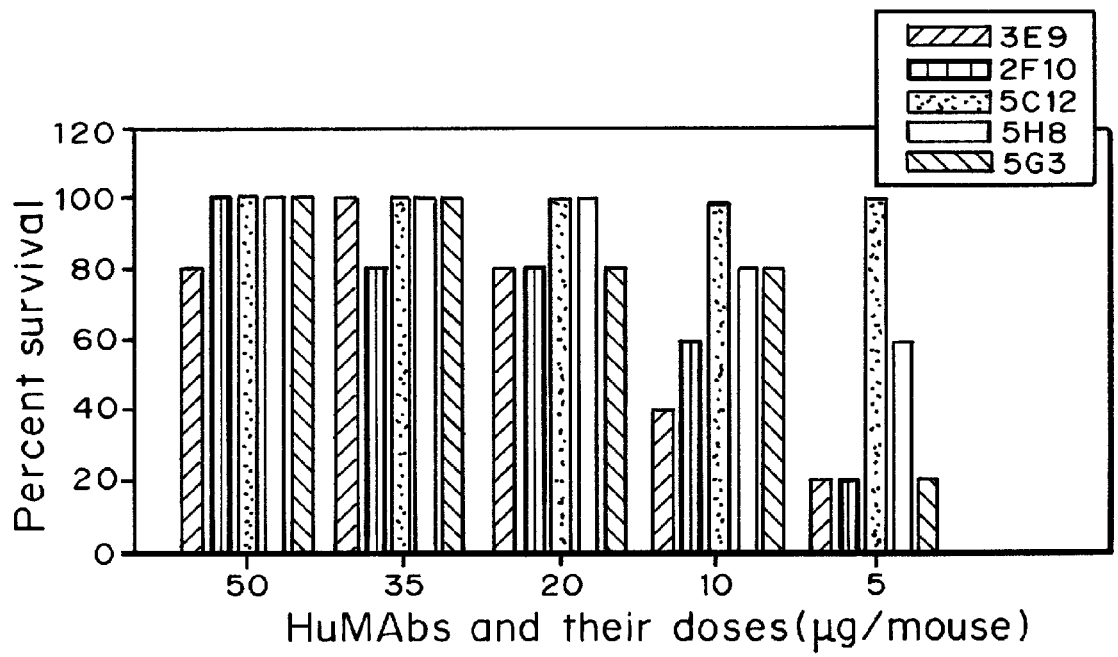
FIG. 7 is a graph of the percent survival of mice given i.p. 50, 35, 20, 10, or 5 µg of HuMAbs 3E9, 2F10, 5C12, 5H8, or 6G3 followed 18 h later with i.p. administration of a 250% lethal dose of Stx2. Mice in PBS and IgG1(κ) control groups died within 3 days of Stx2 injection. All HuMAbs protected mice but showed dose dependency except 5C12, which protected 100% of the mice even at the lowest dose administered (5 µg/mouse).

Protection of Gnotobiotic Piglets Infected with E. Coli 0157:H7 by Administration of Hu-mAb 24 and 48 Hours after Infection The results shown above demonstrate the administration of Hu-mAb significantly protects gnotobiotic piglets infected with E. coli 0157:H7 when the antibodies are administered 6 or 12 hours following infection. The effect of antibodies are administered 6 or 12 hours following infection. The effect of treatment of infected piglets with Hu-mAbs at 24 and 48 hours after infection was then tested. At 48 hours after bacterial infection, piglets have diarrhea for at least 24 hours and are at, or close to, the onset of CNS symptoms. The results are shown in FIG. 5. The data demonstrate the treatment of infected piglets with Hu-mAbs at 24 and 48 hours after infection significantly protects the piglets. When the data are taken together, only 1 of 24 piglets treated with control IgG/PBS survived (4%), while 21 of 24 piglets treated with 5C12 Hu-mAb survived (87%).

TABLE 5

Effect of administration of Stx2 Hu-mAb 24 or 48 hours after infection of gnotobiotic piglets with E. coli O157:H7

| Treatment | Dose (hr. post-infection) | Number of piglets | Piglets survived (percent survival) | Serun conc. (µg/ml)[1] |
|---|---|---|---|---|
| 5C12 | 1.5 mg (24 hr) | 7 | 6 (86) | 3.0 ± 1.8 |
| PBS | 0 | 7 | 0 (0) | 0 |
| 5C12 | 3 mg (24 hr) | 9 | 7 (77) | 4.4 ± 10 |

TABLE 4

Effect of Stx2 Hu-mAb administration on gnotobiotic piglets infected with strain 86-24

| Exp. #[a] | Treatment Group | Hu-mAb Dose (mg) | Timing (hours post-infection) | CNS Signs[b] | CNS Lesions[c] | Survival[d] Avg. ± S.D. (days) | p-value | n | Average Serum Human IgG Level ± S.D. (µg/ml) |
|---|---|---|---|---|---|---|---|---|---|
| 104 | PBS | 0 | 6 | 3/4 | 3/4 | 3.8 ± 2.08[f] | — | 5 | ND[g] |
|  | 3E9 | 3 | 6 | 0/5 | 0/5 | 6.7 ± 2.08[f] | 0.044 | 5 | 4.91 ± 2.8 |
|  | 5H8 | 3 | 6 | 0/2 | 0/2 | 7.0 ± 0[f] | 0.083 | 2 | 3.84 ± 0 |
| 117 | PBS | 0 | 12 | 2/2 | 2/3 | 6.67 ± 1.53 | — | 3 | ND[g] |
|  | 3E9 | 3 | 12 | 0/4 | 0/4 | 10.0 ± 0[f] | 0.016 | 4 | 5.16 ± 2.8 |
|  | 5H8 | 3 | 12 | 0/3 | 0/3 | 10.0 ± 0[f] | 0.029 | 3 | 2.82 ± 0.4 |
| 115 | PBS | 0 | 12 | 3/3 | 3/3 | 3.83 ± 1.04 | — | 3 | ND[g] |
|  | 2F10 | 3 | 12 | 0/3 | 1/4[e] | 6.0 ± 1.35[f] | 0.068 | 4 | 8.85 ± 2.1 |
| 128 | PBS | 0 | 12 | 5/5 | 5/5 | 3.2 ± 0.98 | — | 5 | ND |
|  | 5C12 | 3 | 12 | 0/4 | 0/4 | 8.6 ± 3.13 | 0.005 | 5 | 4.81 ± 6.97 |

[a]Experiments 104, 115, 117 and 128 were terminated on days 7, 8, 10, and 10, respectively.
[b]CNS signs included paddling, head-pressing, seizures, opisthotonous, and/or ventrally fixed eye deviation. Only piglets observed immediately prior to death or euthanasia were included in observations.
[c]CNS lesions included hemorrhage and edema present within histopathological sections of the cerebrum and/or cerebellum.
[d]Average survival of gnotobiotic piglets following administration of 3 mg Hu-mAb 6 or 12 hours following oral infection with E. coli O157:H7 strain 86-24. All piglets which died or were euthanized due to experimental manipulations were included in the survival data. p-values were calculated for the comparison of average survival of PBS control groups and Hu-mAb treated groups by parametric (log-rank) and non-parametric (Wilcoxon) analyses. Comparable p-values were obtained with both analyses. The table shows p-values obtained by log-rank analysis.
[e]The lesions present within the CNS tissue of one piglet within this group were very mild and thus not conclusive. Nonetheless, the piglet was included with those that had definite lesions.
[f]Average includes censored data points, i.e. animals alive at the termination of the experiment. Analysis accounted for censored observations (animals alive at termination of experiment) and thus estimate of the mean in these groups is biased against prolongation of survival.
[g]ND = not detectable
[h]NA = not available

TABLE 5-continued

Effect of administration of Stx2 Hu-mAb 24 or 48 hours after infection of gnotobiotic piglets with *E. coli* O157:H7

| Treatment | Dose (hr. post-infection) | Number of piglets | Piglets survived (percent survival) | Serum conc. (μg/ml)[1] |
|---|---|---|---|---|
| IgG/PBS | 0 | 10 | 1 (10) | $9.2 \pm 2.5$[2] |
| 5C12 | 6 mg (48 hr) | 8 | 8 (100) | $16.9 \pm 7.4$ |
| PBS | 0 | 7 | 0 (0) | 0 |

[1]The isotype of 5C12 is human IgG1, and serum concentration of human IgG1 is shown.
[2]Myeloma human IgG1 (Sigma) was given as control to 8 piglets.

Efficacy of Stx2-Specific Hu-mAbs Against Clinical Isolates

An in vitro cytotoxicity assay was utilized to determine the relative efficacy of the Stx2-specific Hu-mAbs, 2F10, 3E9, 5C12, 5H8, and 6G3 against Stx2 and/or Stx2 variants (i.e., Stx2a, Stx2, Stx2b) produced by 30 EHEC strains. A neutralization index representing the amount of Stx2 neutralized was determined for each Stx2-specific Hu-mAb-strain combination (Table 6). This neutralization index was plotted as a function of the type of Stx2 produced by the EHEC strain in an effort to compare the efficacy of each Stx2-specific Hu-mAb against the various types of Stx2 (FIG. 2). The neutralization index is a function of both the ability of Hu-mAb to bind the Stx present as well as the amount of Hu-mAb needed to neutralize the cytotoxicity of the Stx present.

Both the Stx2 A-subunit specific (2F10, 3E9, 5C12) and B-subunit specific (5H8, 6G3) Hu-mAbs effectively neutralized the cytotoxic activity of culture supernatants containing Stx2 alone. Hu-mAbs 2F10, 5C12, and 6G3 were most effective against Stx2-containing culture supernatants (neutralization indices >0.5 for all 17 supernatants). In contrast, neutralization indices of <0.5 were observed for Hu-mAbs 3E9 and 5H8 for 1-4 of these Stx2-containing culture supernatants.

Each of the Stx2 A-subunit specific Hu-mAbs 2F10, 3E9, and 5C12 effectively neutralized the cytotoxic activity of 6 of 7 culture supernatants containing Stx2a. Each of these Hu-mAbs was ineffective against the Stx2a produced by EHEC strain 91-8076 (Table 6). Although the toxin profile of each strain was determined by PCR prior to use in this assay, it is possible that the Stx2 produced by EHEC strain 91-8076 was either structurally somewhat different than the Stx2 produced by the other Stx2-producing EHEC strains or that an additional cytotoxic entity, such as Stx1 was indeed produced by this strain. The Stx2 B-subunit specific Hu-mAbs 5H8 and 6G3 exhibited lesser activity against these Stx2a-containing culture supernatants-5H8 exhibited no activity any of the 7 culture supernatants and 6G3 exhibited little or no activity. Given that these B-subunit specific Hu-mAbs were effective against Stx2 but not Stx2a-containing culture supernatants indicates that the structural differences between Stx2 and Stx2a significantly impacted the efficacy of the B-subunit specific Hu-mAbs. Furthermore, the differential activity of these Stx2 B-subunit specific Hu-mAbs against the Stx2-containing culture supernatants suggests differences in epitope specificity between Hu-mAbs 5H8 and 6G3.

Variable efficacy was exhibited against culture supernatants containing Stx2+Stx2a. Both Stx2 A and B subunit specific Hu-mAbs were effective against the Stx2 and Stx2-producing EHEC strains 92-9199, 95-8112, 97-8037. However, only the A-subunit specific Hu-mAbs 2F10 and 3E9 exhibited activity against EHEC strain 97-8075.

The Stx2 A-subunit specific Hu-mAbs, 2F10, 3E9, and 5C12, were effective against the Stx2b-producing strain, 95-0243 and the Stx2c-producing strains E32511 and pJH. In contrast, the Stx2 B-subunit specific Hu-mAbs 5H8 and 6G3 were ineffective against these strains. Furthermore, none of the Stx2-specific Hu-mAbs were effective against EHEC strain 95-0459 which produces Stx2+Stx2b.

Overall, based on the spectrum of activity against the Stx2 and Stx2 variants produced by the EHEC strains utilized, the relative efficacy of the Stx2-specific Hu-mAbs is: 2F10>3E9>5C12>6G3>5H8 (FIG. 2). Thus, A-subunit specific Hu-mAbs appear to be superior to B-subunit specific Hu-mAbs. Amongst the A-subunit specific Hu-mAbs, 2F10, 3E9, and 5C12, Hu-mAb 5C12 appears to be the most potent, i.e. for those culture supernatants which it exhibits neutralizing ability, the amount of toxin neutralized is greater than when in the presence of Hu-mAbs 2F10 or 3E9.

TABLE 6

Neutralization indices of of Stx2-Specific Hu-mAbs[a].

| EHEC Strain | Toxin Profile of EHEC Strain | Stx2-Specific Hu-mAb | | | | |
|---|---|---|---|---|---|---|
| | | 2F10 (anti A) | 3E9 (anti A) | 5C12 (anti A) | 5H8 (anti A + B) | 6G3 (anti A + B) |
| 91-8000 | Stx2 | 0.68 | 0.45 | 1.16 | 0.35 | 0.56 |
| 91-8069 | Stx2 | 0.9 | 0.93 | 1.52 | 0.85 | 1.1 |
| 92-9035 | Stx2 | 0.95 | 0.66 | 1.19 | 0.43 | 0.87 |
| 93-8059 | Stx2 | 1.15 | 0.72 | 1.09 | 1.37 | 1.05 |
| 93-8073 | Stx2 | 1.0 | 0.82 | 1.43 | 0.86 | 0.95 |
| 93-8094 | Stx2 | 0.64 | 0.6 | 1.4 | 0.9 | 0.99 |
| 93-8127 | Stx2 | 0.77 | 0.88 | 1.1 | 0.68 | 1.25 |
| 93-8132 | Stx2 | 0.78 | 0.51 | 1.15 | 0.94 | 1.05 |
| 93-8176 | Stx2 | 0.88 | 0.71 | 0.9 | 0.56 | 1.02 |
| 94-9004 | Stx2 | 1.33 | 0.95 | 1.42 | 0.77 | 1.13 |
| 94-9028 | Stx2 | 1.03 | 0.66 | 1.12 | 0.62 | 0.99 |
| 94-9038 | Stx2 | 0.81 | 0.77 | 1.13 | 0.45 | 1.29 |
| 94-9050 | Stx2 | 1.04 | 0.62 | 0.77 | 0.81 | 1.33 |
| 94-9059[b] | Stx2 | 0.77 | 1.06 | 1.2 | 0.53 | 1.06 |
| 95-8049 | Stx2 | 0.66 | 0.6 | 1.16 | 0.75 | 0.93 |
| 95-8080 | Stx2 | 1.1 | 0.66 | 1.32 | 0.72 | 0.75 |
| 96-9102 | Stx2 | 0.76 | 0.64 | 1.12 | 0.44 | 1.03 |
| 91-8076[b] | Stx2a | 0 | 0 | 0 | 0 | 0.13 |
| 91-8099 | Stx2a | 1.22 | 0.74 | 1.26 | 0 | 0 |
| 92-9140 | Stx2a | 0.96 | 0.61 | 1.3 | 0 | 0 |
| 93-8021 | Stx2a | 1.14 | 0.4 | 0.93 | 0 | 0.38 |
| 93-8053 | Stx2a | 1.07 | 0.15 | 0.35 | 0 | 0.32 |
| 94-8055 | Stx2a | 0.9 | 0.56 | 1.02 | 0 | 0 |
| 95-8061 | Stx2a | 0.76 | 0.62 | 0.4 | 0 | 0.19 |
| 92-9199 | Stx2 + Stx2a | 0.6 | 0.8 | 1.0 | 0.5 | 0.93 |
| 95-8112 | Stx2 + Stx2a | 0.8 | 0.8 | 0.97 | 0.67 | 1.05 |
| 97-8037 | Stx2 + Stx2a | 0.84 | 0.77 | 1.36 | 0.49 | 1.02 |
| 97-8075[c] | Stx2 + Stx2a | 1.12 | 0.8 | 0 | 0 | 0 |
| 95-0243 | Stx2b | 0.73 | 0.67 | 0.62 | 0 | 0 |
| 95-0459[c] | Stx2 + Stx2b | 0 | 0 | 0 | 0 | 0 |
| E32511 | Stx2c | 0.72 | 0.75 | 1.15 | 0 | 0 |
| pJH | Stx2c | 0.99 | 0.73 | 1.12 | 0 | 0 |

[a]Neutralization index is defined as the $\log_{10}$ of the dilution of Stx-containing culture supernatant neutralized by 1.25 .mu.g/ml Stx2-specific Hu-mAb.
[b]On retyping, strains found to produce both Stx 1 and Stx2; retyping experiments to be reconfirmed.
[c]On retyping, strains found to produce both Stx1 and Stx2; also preliminary evident of production of Stx2c.

Factors Affecting Therapeutic Efficacy in Hemolytic Uremic Syndrome

Numerous epidemiological studies support the observation that Shiga-like toxin II (Stx2) exceeds Shiga like toxin I as a causative factor in hemolytic uremic syndrome. As described above, selected human monoclonal antibodies were shown to have superior neutralization ability for Stx2 and variants of Stx2 as described in the previous section (Table 6). It is noted that the human monoclonal antibodies with superior neutralization ability neutralize the toxin A-subunit only. Note especially the antibodies 5C12, 3E9 and 2F10. Simultaneous affinity against the toxin B-subunit may block neutralization in some Stx2 variants. Note the antibodies 5H8 and 6G3. Accordingly, the most preferred antibodies are those human monoclonal antibodies that bind the A-subunit of Stx2 and that neutralize the greatest number of Stx2 variants.

Example 4

Dose Response Study in Gnobiotic Piglets

Infection of children with Shiga toxin (Stx)-producing Escherichia coli (STEC) leads to hemolytic-uremic syndrome (HUS) in 5 to 10% of patients. Stx2, one of two toxins liberated by the bacterium, is directly linked with HUS. As demonstrated above, Stx-specific human monoclonal antibodies protect STEC-infected animals from fatal systemic complications. The present study defines the protective antibody dose in relation to the time of treatment after the onset of diarrhea in infected gnotobiotic piglets. Using the mouse toxicity model, 5C12, an antibody specific for the A subunit, was selected as the most effective Stx2 antibody for further characterization in the piglet model in which piglets developed diarrhea 16 to 40 h after bacterial challenge, followed by fatal neurological symptoms at 48 to 96 h. Seven groups of piglets received doses of 5C12 ranging from 6.0 mg/kg to 0.05 mg/kg of body weight, administered parenterally 48 h after bacterial challenge. The minimum fully protective antibody dose was 0.4 mg/kg, and the corresponding serum antibody concentration in these piglets was 0.7 µg (±0.5)/ml, measured 7 to 14 days after administration. Of 40 infected animals which received Stx2 antibody treatment of ≧0.4 mg/kg, 34 (85%) survived, while only 1 (2.5%) of 39 placebo-treated animals survived. This demonstrates that the administration of the Stx2-specific antibody was protective against fatal systemic complications even when it was administered well after the onset of diarrhea and indicate that children treated with this antibody, even after the onset of bloody diarrhea, should be equally protected against the risk of developing HUS.

Materials and Methods

Bacteria and toxin. Enterohemorrhagic E. coli O157:H7 strain 86-24, which produces Stx2, was isolated in 1986 from a patient in Seattle, Wash. (Tarr, et al. 1989. J. Infect. Dis. 159:344-347). Purified Stx2 was obtained as described by Donohue-Rolfe, et al. 1989. Infect. Immun. 57:3888-3893).

Stx2-specific HuMAbs. The production of 37 hybridomas secreting Stx2-specific HuMAbs (Mulherjee, et al. 2002. Infect. Immun. 70:612-619), from which five HuMAbs were selected for further evaluation, is described above. Three HuMAbs against the A subunit (3E9, 2F10, and 5C 12) and two against both the A and the B subunits (5H8 and 6G3) were selected (Sheoran, et al. 2003. Infect. Immun. 71:3125-3130)). All five HuMAbs were of the human immunoglobulin G1(κ) [IgG(κ)] isotype. HuMAbs were used either in the form of mouse ascites or as concentrated protein-free cell culture media (HyQ ADCF-MAb; HyClone, Logan, Utah) in CELLine 1000 flasks (BD Biosciences, Bedford, Mass.).

Quantitation of Stx2-specific HuMAbs by enzyme-linked immunosorbent assay. The IgG1 (κ) concentration of each HuMAb in mouse ascites fluid and from CELLine 1000 flasks was measured by enzyme-linked immunosorbent assay. Briefly, 96-well plates were coated overnight at 4° C. with 100 µl of the mouse anti-human κ light-chain MAb at 2.5 µg/ml. Plates were washed with phosphate-buffered saline-Tween 20 (PBS-T; PBS, 0.05% Tween 20) and blocked with 100 µl/well of 2% nonfat dried milk powder in PBS-T at 37° C. Following washing, samples (ascites fluid or cell culture supernatants or pig serum) diluted 1:10 or 1:100 in PBS-T were diluted serially twofold in duplicate rows of the plate (100 µl/well). The human IgG1(κ) (Sigma, St. Louis, Mo.) standard was similarly titrated on each plate from a starting concentration of 1 µg/ml. The plates were incubated at 37° C. for 1 h and washed again. Horseradish peroxidase-conjugated goat anti-human IgG (Southern Biotech, Birmingham, Ala.), which is affinity purified and cross-adsorbed with human IgA, IgM, and IgD, was added at 100 µl/well at a dilution of 1/1,000. Following incubation at 37° C. for 1 h and washing, the plates were developed with substrate solution (0.2% o-phenylenediamine, 0.05% hydrogen peroxide in citric acid-phosphate buffer, pH 5.0). The chromogenic reaction was stopped using 50 µl of 2 M sulfuric acid, and the absorbance was read at 490 µm. Using the linear portion of the IgG1(κ) standard curve, the total IgG1(κ) content of each HuMAb was determined and expressed as mg or µl of IgG1(κ)/ml.

HeLa cell cytotoxicity neutralization assay. The in vitro HeLa cell cytotoxicity assay was used to evaluate the efficacy of each HuMAb to neutralize the toxic effects of Stx2 exerted against HeLa cells. Briefly, HeLa cells were plated at 1.4× $10^4$/well on 96-well plates in McCoy's 5A medium (Mediatech, Inc., Herndon, Va.) containing 10% fetal bovine serum (Harlan Bioproducts for Science, Inc., Madison, Wis.) and incubated overnight at 37° C. in 5% $CO_2$. Stx2 was titrated on HeLa cells to determine the concentration that killed ~70% of HeLa cells. Dead cells were removed by washing with PBS, and crystal violet was used to stain viable cells (Keusch, et al. 1988. Methods Enzymol. 165:152-162). Stx2 at a dilution that killed ~70% of HeLa cells was preincubated with the HuMAbs or Fab fragments at various concentrations for 1 h at 37° C. in 5% $CO_2$ and then added to the cells and incubated overnight at 37° C. in 5% $CO_2$. Plates were developed by crystal violet staining, and the absorbance (optical density [OD]) was read at 690 nm. The percent neutralization of Stx2-mediated HeLa cell cytotoxicity by the HuMAbs was calculated by the following formula: $[(OD_{toxin+HuMAb} - OD_{toxin\ only})/(OD_{no\ toxin} - OD_{toxin\ only})] \times 100$, where the ODs were determined for plates containing toxin and HuMAb, toxin only, and no toxin.

Mouse toxicity model. The mouse toxicity model (Islam, et al. 1990. J. Clin. Lab. Immunol. 33:11-16.) was used to select the most protective among the five HuMAbs against a lethal Stx2 dose in mice. Dose-response studies were performed with groups of five 3- to 4-week-old, female Swiss Webster mice (Taconic) to determine the amount of Stx2 required to induce 100% mortality in untreated animals. A concentration of 25 ng of Stx2 was sufficient (data not shown). The efficacies of the HuMAbs were evaluated by administering every Stx2-specific HuMAb intraperitoneally (i.p.) to each of the five 3- to 4-week-old Swiss Webster mice at a dose of 5, 10, 20, 35, or 50 µg/mouse in 200 µl of PBS followed 18 h later by i.p. administration of 62.5 ng (250% lethal dose) of Stx2. A control group of five mice received human myeloma IgG1(κ) (20 µg/mouse; Sigma, St. Louis, Mo.), and another control group received 200 µl of PBS alone. Both control groups were also challenged with 62.5 ng of Stx2. The mice were observed twice daily for survival.

Gnotobiotic piglet model of E. coli STEC infection. The selected antibody, 5C12, was then further characterized in the gnotobiotic piglet model of STEC infection, previously described, using E. coli strain 86-24 (Mukherjee, et al. 2002. Infect. Immun. 70:612-619). A total of 117 piglets were used to determine the minimum protective dose of the HuMAb 5C 12, given i.p., either 24 h (17 treated, 17 placebo) (Table 9) or 48 h (39 treated, 44 placebo) (Table 10) after bacterial challenge with ~$10^{10}$ CFU of strain 86-24. This large inoculum usually induces neurological signs and lesions associated with Stx2 activity in approximately 90% of control piglets within 48 to 96 h postinfection (Donohue-Rolfe, et al. 2000. J. Infect. Dis. 181:1825-1829). The placebo group received either human myeloma IgG1(κ) (Sigma, St. Louis, Mo.) or PBS. Piglets were monitored several times daily for symptoms of diarrhea, dehydration, and CNS complications, which included ataxia, paresis, headpressing, paddling, convulsions, and opisthotonos. Piglets were rehydrated i.p. twice daily (20 to 30 ml/injection) with Aminosyn II 3.5% M plus 5% Dex Inj NTRMX (Hospira, Ill.), an amino acid injection with maintenance electrolytes in a dextrose injection, immediately after the appearance of diarrhea. Surviving animals with severe CNS symptoms, or animals that survived 7 to 14 days after the bacterial challenge, were humanely euthanized. Animals that succumbed before administration of the antibody were excluded from analysis. Those animals were not part of the 117 piglets included in this study. Brain tissue (cerebral cortex and cerebellum) and gut sections were fixed in formalin and processed for histology, and blood was collected for measuring serum antibody concentration.

Table 7 shows survival of piglets treated i.p. with 5C12 antibody or control after oral challenge with STEC 86-24, an Stx2 producer. Table 8 shows survival of piglets orally challenged with $10^{10}$ CFU of STEC 86-24 followed by i.p. administration of PBS (placebo) or 5C12 antibody at 48 h after bacterial challenge.

TABLE 7

Survival of piglets treated i.p. with 5C12 antibody or control after oral challenge with STEC 86-24, an Stx2 producer[a]

| Treatment type | Antibody concn (mg/kg) | Total no. of piglets | No. (%) of surviving piglets[b] | Serum IgG1(κ) concn (μg/ml)[c] |
|---|---|---|---|---|
| 5C12 | 3 | 9 | 7 (78) | 4.4 ± 1.0 |
| IgG1κ | 3 | 8 | 0 (0) | 9.2 ± 2.5 |
| PBS | 0 | 2 | 1 (50) | 0 |
| 5C12 | 1.5 | 8 | 6 (75) | 3.1 ± 1.8 |
| PBS | 0 | 7 | 0 (0) | 0 |

[a]Irrelevant human IgG(κ) or PBS was used as the control. Challenge was with $10^{10}$ CFU of STEC 86-24.
[b]Piglets were either euthanized due to severe CNS-related illness or found dead.
[c]Results reflect the concentration in serum

TABLE 8

Survival of piglets orally challenged with $10^{10}$ CFU of STEC 86-24 followed by i.p. administration of PBS (placebo) or 5C12 antibody at 48 h after bacterial challenge

| Treatment | Dose (mg/kg) | Total no. of piglets | No. (%) of surviving piglets[a] | Days of survival after infection (mean ± SD)[b] | Serum IgG1(κ) concn (μg/ml)[c] |
|---|---|---|---|---|---|
| 5C12 | 6 | 8 | 8 (100) | | 16.9 ± 7.4 |
| Placebo | 0 | 7 | 0 (0) | 4.6 (±1.9) | 0 |
| 5C12 | 3 | 4 | 4 (100) | | 11.4 ± 1.2 |
| Placebo | 0 | 3 | 0 (0) | 4.6 (±0.6) | 0 |
| 5C12 | 0.75 | 6 | 5 (83) | 3.0 | 2.0 ± 1.2 |
| Placebo | 0 | 5 | 0 | 3.4 (±0.5) | 0 |
| 5C12 | 0.4 | 5 | 4 (80) | 4.0 | 0.7 ± 0.5 |
| Placebo | 0 | 7 | 0 | 3.4 (±0.5) | 0 |
| 5C12 | 0.2 | 5 | 1 (20) | 4.0 (±1.4) | 0.6 ± 0.1 |
| Placebo | 0 | 6 | 0 | 3.5 (±0.8) | 0 |
| 5C12 | 0.1 | 7 | 4 (57) | 7.0 (±3.4) | 0.18 ± 0.04 |
| Placebo | 0 | 8 | 0 | 4.2 (±1.7) | |
| 5C12 | 0.05 | 4 | 1 (25) | 7.0 (±3.4) | 0.07 ± 0.03 |
| Placebo | 0 | 8 | 0 | 4.2 (±1.7) | |

[a]Piglets that did not survive either died overnight or were euthanized due to severe illness.
[b]Data for surviving piglets in the 5C12 group who were euthanized at the end of the experimental period (7 to 14 days) are included. Data for the piglets who were euthanized or died in the 5C12 group at another time are not included.
[c]Results reflect the concentration in serum of the human IgG1(κ) isotype, which is the isotype of 5C12. Values are means ± standard deviations.

Affinity determination of HuMAbs. The binding kinetics of the HuMAbs with Stx2 were determined by surface plasmon resonance (BIACore 3000; Biacore Inc., Piscataway, N.J.) using the procedure of indirect capture of MAbs (Myszka, D. G 1999. J. Mol. Recognit. 12:279-284; Pless, et al. 2001. Infect. Immun. 69:570-574). Rabbit anti-human IgG Fc (Jackson Immuno Laboratories, West Grove, Pa.) was amine coupled to a CM5 (carboxymethylated dextran matrix) chip as the capture antibody, and then the HuMAb to be tested was run over it. The capture antibody and the HuMAb complex remained stable over the duration of each run. Kinetics analysis was performed at a flow rate of 100 μl/min to reduce mass transport limitations. Injections were performed with twofold dilutions in duplicate, with Stx2 concentrations ranging from 100 nM to 6.25 nM in HEPES-buffered saline with 3 mM EDTA and 0.005% Tween 20. The surface was regenerated with 4 M $MgCl_2$ to disrupt the interaction between the capture antibody and the HuMAb before the HuMAb was reapplied for the next run.

Results

Concentration of HuMAbs in ascites fluid and in concentrated cell culture supernatant. Since the five HuMAbs were produced at only ng/ml quantities by conventional tissue culture propagation of hybridomas in 75-$cm^2$ flasks, they were produced as ascites fluid for mouse toxicity and in vitro neutralization assays. The mean concentrations of 5H8, 6G3, 3E9, 2F 0, and 5C12 in ascites fluid were 1.8 mg/ml, 308 μg/ml, 532 μg/ml, 226 μg/ml, and 459 μg/ml, respectively. For the experiments with piglets, 5C12 was produced as concentrated cell culture supernatant in CELLine 1000 flasks (BD Biosciences, Bedford, Mass.). The mean concentration of 5C 12 in cell culture supernatant was 250 μg/ml.

Antibody neutralization of Stx2 in HeLa cells. All HuMAbs completely neutralized cytotoxicity at the highest concentration of 5 μg/ml, except HuMAbs 3E9 and 6G3, which manifested partial neutralization (FIG. 1). Differences in neutralizing efficiency were apparent in all HuMAbs at lower doses. As FIG. 1 indicates, at 8 ng/ml, 5C12, reactive with the A subunit, was superior among the five HuMAbs tested, with 40% neutralization of Stx2 cytotoxicity for HeLa cells.

Antibody neutralization of Stx2 in the mouse assay. Although all five HuMAbs were effective at protecting mice against a lethal dose of Stx2, differences in relative potency were apparent at the lowest doses of 10 and 5 μg/mouse (5C12>5H8>6G3=2F10=3E9) (FIG. 8). 5C12, directed against the A subunit of the toxin, was the most effective, protecting all five mice at the lowest dose of 5 μg/mouse. Although less effective at 5 μg/mouse, 5H8, which is directed against the B subunit, showed results indicating that antibodies against both toxin subunits are capable of effective neutralization in vivo. Percent survival of mice given i.p. 50, 35, 20, 10, or 5 μg of HuMAbs 3E9, 2F10, 5C12, 5H8, or 6G3 followed 18 h later with i.p. administration of a 250% lethal dose of Stx2. Mice in PBS and IgG1(κ) control groups died within 3 days of Stx2 injection. All HuMAbs protected mice but showed dose dependency except 5C12, which protected 100% of the mice even at the lowest dose administered (5 μg/mouse).

Affinity of the HuMAbs. Affinities of the Stx2 A subunit-specific HuMAbs were in the order of 2F10>3E9>5C12 (Table 8). The HuMAb 2F 10 had Stx2-binding kinetics of $k_{on}$ (association rate) equal to 2.3×105 $M^{-1}s^{-1}$ and $k_{off}$ (dissociation rate) equal to 8.8×10$^{-5}$ s$^{-1}$, giving a $K_d$ of 0.39 nM. The HuMAbs 3E9 and 5C12 had 1.7- and 2.17-fold higher $K_d$s, respectively.

Table 9 shows the relative affinities of three HuMAbs against the alpha subunit of Stx2.

TABLE 9

Relative affinities of three HuMAbs directed against the A subunit of Stx2

| HuMAb | $k_{off}$ | $k_{on}$ | $K_d$ (nM) |
|---|---|---|---|
| 2F10 | 8.8 × 10$^{-5}$ | 2.3 × 10$^5$ | 0.39 |
| 3E9 | 4.3 × 10$^{-5}$ | 6.2 × 10$^4$ | 0.69 |
| 5C12 | 1.1 × 10$^{-4}$ | 1.3 × 10$^5$ | 0.85 |

Experiments with 5C12 in gnotobiotic piglets. Animals that either died or became severely ill and were euthanized before the onset of treatment at 48 h were excluded from this investigation. Piglets received antibody treatment either 24 h (Table 9) or 48 h (Table 10) after bacterial challenge. This was well after the onset of diarrhea in all animals but before or at onset of CNS symptoms. Table 9 shows that treatment with 5C12 at either 1.5 or 3 mg/kg of body weight administered 24 h after challenge was protective (78% and 75%, respectively), compared with treatment with the placebo. The placebo for the 3-mg/kg group included an equal dose (3 mg/kg) of an irrelevant human IgG1(κ) given i.p. to eight animals, which showed that a specific antibody against Stx2 was needed for protection against challenge with STEC. Because of the expense involved, all subsequent experiments were performed using PBS as the placebo.

Table 10 summarizes the dose response of piglets given doses of 5C12 ranging from 6 mg/kg down to 0.05 mg/kg and challenged 48 h later. When administered 48 h after infection, 6 or 3 mg/kg of 5C12 protected all piglets against fatal systemic complications. The corresponding mean serum concentrations of antibody were 16.9 and 11.4 μg/ml, respectively. The lowest protective dose was 0.4 mg/kg, with a corresponding mean serum concentration of 0.7 μg/ml. The doses below 0.4 mg did not provide reliable protection. The mean survival time of piglets in the PBS control groups ranged from 3.4 to 4.6 days. Two of 23 piglets in groups which received ≧0.4 mg/kg of 5C12 succumbed (91% survival rate), while 10 of 16 piglets in the groups which received ≦0.2 mg/kg 5C12 succumbed (37% survival rate). The mean survival time of piglets that received ≦0.2 mg/kg 5C12 ranged from 4.0 to 7.0 days (Table 10). When the results of Tables 9 and 10 are combined, 34 of the 40 animals (85%) that received ≧0.4 mg/kg of 5C12 survived STEC challenge, while only 1 (2.5%) of 39 piglets which the received placebo of either irrelevant human antibody (8 animals) or PBS (31 animals) survived.

Clinical observations. Piglets challenged orally with STEC typically develop profound GI tract symptoms within 2 days, including diarrhea, anorexia, depression, dehydration, and moderate but rapid loss of body weight. To avoid mortalities due to dehydration, all piglets received supplemental fluid therapy at and subsequent to the onset of diarrhea. Of the 83 piglets (Table 10) which had received the antibody or placebo at 48 h after bacterial challenge, 38 developed GI tract symptoms within 24 to 26 h, and all 83 developed them within 40 h of infection. This shows that all animals had serious GI tract symptoms that required rehydration well before the onset of antibody therapy at 48 h. As expected, while parenteral administration of Stx2 antibody had a major impact on animal survival, it had no effect on the severity of the GI tract symptoms (Table 10).

TABLE 10

Dose response in piglets orally challenged with 10$^{10}$ CFU of STEC strain 86-24 and treated 48 h later with 5C12 antibody or placebo[a]

| | Total no. of piglets (no. of piglets euthanized[b] or found dead) with diarrhea onset at: | | | |
|---|---|---|---|---|
| | 16-28 h | | 29-40 h | |
| Treatment | 0.4-6.0[c] | 0.05-0.2 | 0.4-6.0 | 0.05-0.2 |
| 5C12 | 9 (0) | 6 (4) | 14 (2) | 10 (6) |
| PBS | 12 (12) | 11 (11) | 10 (10) | 11 (11) |

[a]All 83 animals developed diarrhea 8 to 32 h before treatment. The time of onset of diarrhea had no impact on the outcome of treatment, nor did antibody therapy improve the severity of the GI tract symptoms (see text).
[b]Severely ill animals were euthanized.

Typically, all piglets challenged with STEC develop diarrhea and other GI tract symptoms due to an intimate attachment of bacteria to the mucosal surfaces of the terminal ileum and the entire large bowel, which include the colon and cecum. The nature, distribution, and extent of the mucosal lesions in gnotobiotic piglets induced by STEC strain 86-24 were consistent with those previously observed (Donohue-Rolfe, A., I. Kondova, S. Oswald, D. Hutto, and S. Tzipori. 2000. *Escherichia coli* O157:H7 strains that express Shiga toxin (Stx) 2 alone are more neurotropic for gnotobiotic piglets than are isotypes producing only Stx1 or both Stx1 and Stx2. J. Infect. Dis. 181:1825-1829; Tzipori, et al 1988. J. Clin. Pathol. 41:1099-1103; Tzipori, et al. 1995. Infect. Immun. 63:3621-3627; Friedrich, et al. 2002. J. Infect. Dis. 185:74-84.

Of the 83 animals whose results are given in Table 10, 16 were found dead in the morning; of these, none were among the piglets which received ≧0.4 mg/kg of antibody, and only 3 were among those which received a lower dose of 5C12. Among the 23 which received ≧0.4 mg/kg of antibody, only 2 were euthanized due to systemic complications (one had neurological symptoms, and another was comatose). In contrast, 18 of the 30 euthanized animals which received the placebo developed typical fatal neurological symptoms of ataxia, paddling, headpressing, and recumbency. The remaining 12 placebo-treated animals were comatose when they were first observed. These neurological symptoms are accompanied histologically by cerebellar vascular lesions of petechial hemorrhages in the molecular and cortex layers, with evidence of infarction and extensive shrinkage of the neuronal nuclei.

Eleven of the surviving antibody-treated animals, kept alive for 14 days after bacterial challenge, continued to have diarrhea but at a reduced intensity after 6 days. They became more alert and very active and gained weight but continued to excrete strain E. coli 86-24 in their feces until euthanasia.

The HuMAb 5C 12 was the most effective among the five HuMAbs selected for initial characterization in cell culture and in the mouse toxicity assay, as shown in the present study. The lowest protective dose when administered 48 h after bacterial challenge or 8 to 32 h after the onset of diarrhea was 0.4 mg/kg of body weight. Doses below 0.4 mg/kg protected some of the animals, indicating that many factors impact the degree of protection observed, including the rate of bacterial colonization and toxin uptake from the gut and the individual genetic variation among outbred animals, among others. Antibody 5C12 was also shown previously to have the widest spectrum of neutralizing activity against Stx2 variants. In these studies, 5C12 protected mice for up to 48 h after oral challenge with STEC strains producing Stx2c, Stx2vha, and Stx2vhb, Sheoran, et al. 2003. Stx2 variants. Infect. Immun. 71:3125-3130.

HUS occurs in 5 to 10% of children with STEC infections, resulting in 5 to 10% of deaths due to renal failure and other complications, including neurological ones (Tzipori, et al. 2004. Clin. Microbiol. Rev. 17:926-941. In earlier studies using the piglet model of STEC, we showed that fatal systemic complications occurred in 90% of animals challenged with the Stx2 producer strain 86-24. In the present study, the mortality rate among the control piglets was close to 100% (1 of 61 survived). Diarrhea in these piglets occurred between 16 and 40 h after bacterial challenge, and fatal systemic complications occurred within 48 to 96 h after challenge. Both results are consistent with earlier observations. In those earlier reports, we described protection of piglets either with five Stx2-specific HuMAbs given i.p. at 12 h (Mukherjee, et al. 2002. Infect. Immun. 70:612-619) or with swine polyclonal antibodies given at 24 h (3) after STEC challenge.

The current study demonstrated that piglets are still fully protected when the interval between bacterial challenge and antibody administration is extended from 12 to 48 h. This is significant since it shows that the administration of 5C12 antibody occurred well after the onset of diarrhea and close to the onset of CNS symptoms. CNS symptoms in piglets are manifestations of the systemic impact of Stx2 uptake from the gut and correspond to the onset of HUS in children. While piglets do not develop the acute kidney lesions attributed to Stx2, which is the hallmark of HUS, they do develop characteristic, vascular system-mediated brain lesions which result in profound and fatal CNS symptoms. Despite this difference, we believe that the piglet model offers several advantages over the infected mouse model. The pathogenic pathways as they relate to Stx2 are similar in humans and pigs, as outlined previously in some detail (Tzipori, et al. 2004. Clin. Microbiol. Rev. 17:926-941). This is particularly relevant to systemic therapy, since the mechanisms and dynamics of toxin uptake from a severely injured colonic mucosa by attaching-effacing bacteria are the same for both species. Consequently, a circulating human antibody that is effective in neutralizing Stx2 in piglets is likely to be even more effective in the homologous human species. The relevance of this model is substantiated further because (i) piglets are the only species in addition to humans that are naturally susceptible to the systemic effects of Stx produced by E. coli organisms that proliferate in the gastrointestinal tract (MacLeod, et al. 1991. Vet. Pathol. 28:66-73; Marques, et al. 1987. FEMS Microbiol. Lett. 44:281-283); (ii) piglets exhibit upon infection with STEC characteristic attaching-effacing lesions in the colonic mucosa (Phillips, et al. 2000. Gut 47:377-381; Tzipori, et al. 1989. Infect. Immun. 57:1142-1150, which are absent in mice (Lindgren, et al. 1993. Infect. Immun. 61:3832-3842); (iii) piglets and humans develop symptoms of diarrhea following infection with STEC, symptoms that the mouse model lacks; (iv) piglets are anatomically and physiologically similar to infants and children; and (v) after the onset of diarrhea, there is a prodromal period in children of 5 to 7 days before the onset of HUS and of about 2 to 3 days in piglets before the onset of CNS symptoms Donohue-Rolfe, et al. 1999. Infect. Immun. 67:3645-3648; Mukherjee, et al. 2002. Infect. Immun. 70:612-619; Tzipori, et al. 2004. Clin. Microbiol. Rev. 17:926-941. We have utilized this window between the onset of diarrhea and the onset of systemic complications in our study because this is the most likely time in which children with bloody diarrhea will be seeking medical intervention. This study showed that piglets were protected when the antibody was administered well after the onset of diarrhea, close to the onset of systemic complications.

The parenteral administration of Stx2 antibody had no effect on the severity or duration of the GI tract symptoms. The 11 antibody-treated animals, while fully protected against systemic complications, continued to have diarrhea and excrete strain 86-24 for at least 14 days. They did not require rehydration therapy 8 to 10 days after bacterial challenge. The results of the in vivo efficacy studies, however, did not correlate with the results of the affinity measurement studies in which the rank order was 2F10>3E9>5C12. This suggests that 5C12 is either directed against an epitope which is more important for functional activity of the toxin or directed more specifically against the "functionally active site" of Stx2 than the epitopes recognized by the other HuMabs. Since 5C12 is directed against the A subunit, it may either inhibit binding of B subunits with $Gb_3$ by stearic hindrance or neutralize its protein synthesis-blocking effect following internalization of the 5C12/Stx2 complex. A clear understanding of the mechanism by which A subunit-specific antibodies neutralize Stx2 in vivo awaits studies on the mechanism of Stx2 neutralization by these HuMAbs and epitope mapping studies. The likely neutralizing mechanism of HuMAbs directed against the B subunit, on the other hand, is most likely blocking of the binding of Stx2 with $Gb_3$.

For affinity measurements of HuMAbs, we preferred capturing the antibody onto the amine-coupled rabbit anti-human IgG Fc over coupling a HuMAb directly onto the chip because the former gives a more uniform and natural orientation since the two Fab arms of every HuMAb are free to interact with the Stx2. Also, since the antibody was reapplied after each run, it was not subjected to regeneration conditions, which are detrimental over time. Lastly, the capture antibody/ HuMAb complex remained stable over the duration of each run and thus did not affect evaluation. Though this method was well suited for affinity measurements of anti-Stx2 A subunit antibodies (2F10, 3E9, and 5C12), it could not measure affinities of the Stx2 B subunit-specific antibodies accurately, because the B subunit is pentameric and therefore pentavalent and can potentially bind with more than one antibody molecule on the chip, producing an avidity effect. For this reason, we have only reported affinity data for the A-subunit binders. It will not be easy to perform affinity measurement studies on B-subunit binders because the recombinant monomeric subunit polymerizes even in the absence of the A subunit.

The observation that a dose of 0.4 mg/kg administered 48 h after bacterial challenge protected piglets suggests that the 5C12-based therapy is more than likely to protect children not only when they present with bloody diarrhea but possibly also when the antibody is given at the onset of HUS. Therefore, the time window of 48 h for immunotherapeutic intervention has direct implications for children at risk of developing HUS, e.g., those presenting with bloody diarrhea or excreting STEC or for contact individuals. The development of rapid and sensitive methods has made it possible to detect STEC infection almost a week before symptoms of HUS become apparent Paton, et al. 1996. J. Clin. Microbiol. 34:1622-1627; Paton, et al. 1999. J. Clin. Microbiol. 37:3357-3361. Adoption of these methods by clinics for diagnosis would greatly benefit immunotherapy. Clinical diagnosis is currently limited to the detection of *E. coli* O157. Since the serum level of 0.7 µg/ml of 5C12 was measured at the time of euthanasia, some 7 to 14 days after antibody therapy, it is well below the expected protective serum level. While not determined, the protective serum level can be extrapolated from half-life studies. An accurate serum protective level should be measured 4 to 6 h after antibody administration.

Stx2 is the most prevalent genotype identified in STEC organisms isolated from patients with HUS (Friedrich, et al. 2002. J. Infect. Dis. 185:74-84; Russmann, et al. 1994. J. Med. Microbiol. 40:338-343; Tzipori, et al. 2004. Clin. Microbiol. Rev. 17:926-941). Stx2c and Stx1, in contrast, are infrequently linked with HUS, and Stx2 variants other than Stx2c are rarely linked with HUS (Ito, H., A. Terai, H. Kurazono, Y. Takeda, and M. Nishibuchi. 1990. Cloning and nucleotide sequencing of Vero toxin 2 variant genes from *Escherichia coli* O91:H21 isolated from a patient with the hemolytic uremic syndrome. Microb. Pathog. 8:47-60; Paton, et al. 1993. Microb. Pathog. 15:77-82; Ramachandran, et al. 2001. J. Clin. Microbiol. 39:1932-1937; Thomas, et al. 1994. Eur. J. Clin. Microbiol. Infect. Dis. 13:1074-1076). Given that STEC can produce any combination of Stx1, Stx2, and/or Stx2c, an ideal therapeutic formulation should, in our view, include antibodies that can neutralize all three, Since 5C12 neutralizes Stx2 and Stx2c, the addition of an antibody against Stx1 to 5C12 will provide the widest spectrum of protection against HUS. We have previously reported the production of several neutralizing Stx1-specific HuMAbs evaluated in the mouse toxicity model (Mukherjee, et al. 2002. Infect. Immun. 70:5896-5899). Such an antibody could be included in future formulations.

In this model, it was possible to reverse the impact of the GI tract symptoms in most piglets by assisted oral feeding and parenteral rehydration. In the current investigation, we made no attempt to reverse the development of systemic complications. All treated animals were given 5C12 antibody before the development of such symptoms. Our approach was intended to mimic the protection of children who may benefit from treatment when they present between the onset of bloody diarrhea and just before hospitalization due to HUS. We do not believe that an antibody is capable of reversing the process of HUS. It may, however, modify the outcome if given early enough. Studies to address this aspect will be conducted with piglets in the future.

In conclusion, the study on the Stx2-specific HuMAb 5C12, which also effectively neutralizes Stx2 variants (Sheoran, et al. 2003. Infect. Immun. 71:3125-3130), protected piglets against fatal CNS symptoms, even when the antibody was administered 48 h after bacterial challenge. The minimum protective dose was established at 0.4 mg/kg body weight. This demonstrates that this antibody, administered at an optimal dose (to be determined in human volunteers) and given immediately after the onset of bloody diarrhea, to patients with confirmed cases of STEC infection, or after exposure to sources contaminated with STEC, will be equally effective in protecting children at risk for developing HUS.

Example 5

Preparation of Specific Human Monoclonal Antibodies Against Shiga-Like Toxin I Using a Transgenic Mouse and Neutralization of this Toxin Using the Monoclonal Antibodies Materials and Methods:
Isolation of Stx1

Stx1 was isolated, purified, and quantified as described previously. Briefly, Stx1 was isolated from *E. coli* strain C600 (933J) which bears the 933J bacteriophage that encodes Stx1. *E. coli* strain C600 (933J) was grown in Modified Syncase Broth at 37° C. with agitation in the presence of 200 ng/ml mitomycin C. Mitomycin C induces the 933J bacteriophage carrying the genes for Stx1. Stx1 was predominately present in the culture supernatant at a yield of ~5 mg/liter. Stx1 in the culture supernatant was precipitated by the addition of 70% ammonium sulfate. The precipitate is dissolved in 10 mM Tris (pH 7.4) and dialyzed against the same buffer. The dialyzed and dissolved precipitate was applied to a Sepharose 4B affinity column containing $P_1$ glycoprotein isolated from *Eichinoccus granuloses* hydatid cysts. The $P_1$ glycoprotein contains an antigenic determinant comprised of the trisaccharide, Gal$\alpha$1-4Gal$\beta$1-4GlcNAc, which specifically binds Stx1 and Stx2. The column was washed extensively with 1 M NaCl to remove contaminating proteins. Stx1 was eluted from the column with 4.5 M $MgCl_2$. The eluted Stx1 was then dialyzed extensively against 20 mM ammonium bicarbonate, lyophilized and stored at −80° C.

Preparation of Stx1 Toxoid

Stx1 toxoid was prepared by formalin treatment of Stx1. Briefly, 100 µg Stx1 was incubated overnight in 5% formalin and then dialyzed extensively against phosphate buffered saline (PBS). Inactivation was confirmed by comparing cytotoxicity of the toxoid versus active Stx1 using HeLa cells (Donohue-Rolfe, et al., *Infect. Immun.*, 57: 3888 to 3893 (1989)).

Generation of Stx1-Specific Hu-Mabs Using Hu-MAb™ Mice

Stx1-specific Hu-mAbs were generated by immunizing mice bearing the HCo12 human heavy chain and HCo5 human light chain immunoglobulin construct with 10-50 µg Stx1 toxoid emulsified in Freund's Complete (initial immunization only) or Incomplete (all subsequent immunizations) Adjuvant i.p. at biweekly intervals a minimum of three times. Serum anti-Stx1 titers were determined by ELISA on microtiter plates coated with 1.5 µg/ml Stx1 and developed with horseradish peroxidase (HRP)-labeled goat anti-human IgG. The spleens of mice with titers≧1:800 were fused to the non-productive murine myeloma, P3×63-Ag8.653, by standard methods. Supernatants from hypoxanthine-aminopterin-thymidine-selected hybridomas were successively screened by ELISA on microtiter plates coated with 1.5 µg/ml Stx1 and developed with horseradish peroxidase (HRP)-labeled goat anti-human IgG or HRP-labeled goat anti-human kappa. Stable, positive clones were selected by subcloning twice by limiting dilution and finally by soft-agar cloning.

Hu-mAb-containing ascitic fluid was prepared by injecting hybridoma cells into the peritoneal cavity of pristane-primed ICR-SCID mice. Hu-mAb concentrations in ascitic fluid were determined relative to those of isotype-matched concentration standards by enzyme-linked immunosorbent assay (ELISA).

Isotype Analysis of Stx1-Specific Hu-mAbs

The isotype of each Hu-mAb was determined by ELISA. Briefly, microtiter plates were coated with 1:1000 dilution goat anti-human kappa and blocked with 1% bovine serum albumin in PBS. Hybridoma culture supernatants or ascitic fluid containing individual Hu-mAbs were plated in each of 8 wells. The eight wells were developed with alkaline phosphatase-labeled anti-human IgM, IgG1, IgG2, IgG3, IgG4, IgA, kappa or lambda followed by addition of 1 mg/ml p-nitrophenyl phosphate. Absorbance at 405 nm was determined.

Analysis of Binding Specificity of Stx1-Specific Hu-mAbs

Stx binding specificity of each Hu-mAb was determined using a sandwich ELISA as follows. Microtiter plates coated with 5 μg/ml of the murine Stx1 or Stx2-specific mabs 4D3 or 3D1 in PBS, were used to capture 1 μg/ml solutions of Stx1 or Stx2, respectively. Hybridoma culture supernatants containing individual Hu-mAbs were plated in duplicate on pairs of plates containing Stx1 or Stx2. Assay was developed with alkaline phosphatase-labeled anti-human kappa followed by addition of 1 mg/ml p-nitrophenyl phosphate. Absorbance at 405 nm was determined.

Subunit-Specificity Analysis of Stx1-Specific Hu-mAbs

The subunit specificity of each Stx1 Hu-mAb was determined by Western blot. Stx1 was cross-linked using the homo-bifunctional cross-linking agent, dimethylpimelimidate to create a mixture containing the A subunit bound to one-five B subunits and B subunit multimers. The cross-linked Stx1 was electrophoresed by SDS-PAGE on a 15% acrylamide slab gel and then electrophoretically transferred to a nylon membrane. Membranes were washed five times with PBS+0.05% TWEEN-20 between each of the following steps. Following electrophoretic transfer, membranes were soaked 1 h in PBS+0.3% TWEEN-20 and then 2 h in PBS+0.05% TWEEN-20+1% BSA. The Surf Blot (model 10.5, Idea Scientific Company, Minneapolis, Minn.) apparatus was used to divide each membrane into 21 discrete lanes. Stx1 Hu-mAbs were incubated at 10 μg/ml in PBS in individual lanes in the presence of membrane-bound Stx1 for 2 hours at room temperature versus the previously described Stx1-specific mouse IgG1 mAb 4D3. A 1:1000 dilution of alkaline phosphatase-labeled anti-Fc reagent specific for the anti-Stx1 mAb present, was added to each lane, i.e. goat anti-mouse IgG1 or goat anti-human IgG, or IgM.

In Vitro Neutralization of Stx1

Two variations of an in vitro cytotoxicity assay were used to evaluate the ability of each Stx1-specific Hu-mAb to neutralize the toxic effects of Stx1 exerted against HeLa cells. For each assay, HeLa cells were plated at $2 \times 10^5$/ml in McCoy's 5A medium+10% fetal calf serum and incubated overnight at 37° C. in 5% $CO_2$. Media was removed prior to addition of Stx1-Hu-mAb mixtures. Each assay was performed independently a minimum of 3 times; the results at a selected data point were averaged. Assay I involved examining the effects of limiting Hu-mAb in the presence of Stx1. Each Hu-mAb was serially diluted 1:2 from 12.5 to 0.0061 μg/ml; each dilution was incubated 30 minutes at room temperature with 10 ng/ml Stx1. Stx1-Hu-mAb mixtures were transferred to HeLa cell monolayers and incubated overnight at 37° C. The relative percent neutralization of 1 ng Stx1 in the presence of 39.1 ng Hu-mAb was determined using a standard curve generated based on the effects of Stx1 alone (Table 6). Assay II involved examining the effects of Hu-mAb in the presence of limiting Stx1. Stx1 was serially diluted 1:2 from 100 to 0.049 ng/ml; each dilution was incubated 30 minutes at room temperature with 1 μg/ml mAb. Stx1-Hu-mAb mixtures were transferred to HeLa cell monolayers and incubated overnight at 37° C. The relative percent neutralization of 0.3125 ng Stx1 in the presence of 100 ng Hu-mAb was determined.

Demonstration of Protective Efficacy In Vivo

A murine Stx1 neutralization assay was used to examine the ability of each Hu-mAb to neutralize the effects of Stx1 in vivo. Dose-response curves were conducted in groups of 3-5 3-4 week old female Swiss Webster mice to determine the amount of Stx1 required to induce 100% mortality in untreated animals (data not shown). Three-four week old female Swiss Webster mice were divided into groups of 6-10. 50 μg Stx2 Hu-mAb in 1 ml PBS or 1 ml PBS (control) was administered i.p. to each of 6-10 3-4-week old Swiss Webster mice followed by i.v. administration of 0.5 μg Stx1 via the lateral tail vein, 18 hours later. Mice were observed twice daily for survival. Experiments were terminated 12 days following Stx1 challenge.

Activity of Stx1 Hu-mAbs Against Stx Produced by Clinical Isolates

An in vitro cytotoxicity assay was utilized to examine the relative efficacy of the Stx1-specific Hu-mAbs against Stx1 produced by a panel of clinical STEC isolates. Two Stx1-specific Hu-mAbs (15G2 and 5A4) were selected for testing. The efficacy of each Stx1-specific Hu-mAb was tested against ten STEC strains each of which produced Stx1 alone.

Culture supernatants containing Stx1 from each STEC strain were prepared. Each assay involved preparing a checkerboard of Stx1-specific Hu-mAb and Stx1-containing culture supernatant dilutions. Following incubation, 150 μl media containing $1.5 \times 10^4$ VERO cells was added to each well. Following 48 h incubation at 37° C., assay was developed and read. The neutralization index was defined as the $\log_{10}$ of the dilution of toxin neutralized by 1.25 μg/ml Hu-mAb.

Results:

Isotype and Subunit Specificity of the Stx1 Hu-mAbs

Eleven stable hybridomas were isolated from transgenic mice bearing the human heavy chain transgenes HCo12 and the human light chain transgene HCo5. Seven of the 11 hybridomas isolated secrete IgMκ Hu-mAbs; 4 secrete IgG1κ Hu-mAbs (Table 6). As determined by ELISA, each hybridoma secretes Hu-mAb specific for Stx1; no cross-reactivity with Stx2 was observed.

The Stx1 subunit specificity of each Hu-mAb was determined by Western blot analysis. Stx1 is comprised of one A subunit of ~32 kD and 5 B subunits each ~7.7 kD (Jackson, Neill, et al. 1987). The A versus B subunit-specificity of the anti-Stx2 Hu-mAbs was determined based on binding to covalently cross-linked Stx1 comprised of a mixture of the A subunit bound to zero-five B subunits and B subunit monomers/multimers. Monoclonal antibodies (mAbs) with specificity for the B subunit bind the B subunit monomers/multimers and the A-B complexes; mAbs with specificity for the A subunit bind the A-B complexes but do not bind B subunit monomers/multimers. The relative intensity of binding is determined not only by whether the particular Stx1 entity is recognized by a mAb but also by the percentage of each complex present within the preparation of cross-linked Stx1. The subunit-specificity of each Stx1-specific Hu-mAb is summarized in Table 6. Consistent with either A or B subunit specificity, all 11 Stx1 Hu-mAbs clearly bound an A-B complex which based on approximate molecular weight corresponds to a complex of the A subunit and one B subunit (A+1B). Ten of the Stx1 Hu-mAbs (1B10, 2D9, 5A4, 8A5, 10F4, 13F1, 14C9, 14H3, 15G2, 15G9) bound entities corresponding to the B subunit monomer (1B) and trimer (3B), indicating specificity for the B subunit. The lack of binding to B subunit monomer/multimers by Stx1 Hu-mAb 7E12 is indicative of specificity for the A subunit. Unexpectedly, the B subunit-specific Stx1 Hu-mAbs also bind the A subunit monomer. This is potentially due to binding an epitope comprised of both A and B subunit moieties.

In Vitro and In Vivo Neutralization of Stx1

The ability of each Stx1 Hu-mAb to neutralize the activity of purified Stx1 was studied using both in vitro HeLa cell cytotoxicity assays and an in vivo murine model of Stx1 neutralization (Table 6). Using the in vitro cytotoxicity assay, the Stx1 Hu-mAb concentration was varied in the presence of a constant amount of Stx1 and the percent of Stx1 neutralized was determined at a single concentration for each Hu-mAb (Table 6).

A murine neutralization assay was used to assess the ability of each Hu-mAb to neutralize Stx1 in vivo. Approximately 18 hours following i.p. administration of 50 µg Hu-mAb, mice were challenged i.v. with 0.5 µg Stx1. The results of both the in vitro and in vivo Stx1 neutralization assays were used to group the Stx1 Hu-mAbs into two categories—those which were highly neutralizing (≧85% neutralization in vitro and prolonged average survival to >10 days; and those which were moderately neutralizing (84-55% neutralization in vivo and prolonged average survival <10 days)). Stx1 Hu-mAbs 2D9, 5A4, 10F4, 15G2, 15G9 were found to be highly neutralizing (Table 6, upper panel); whereas, Stx Hu-mAbs IB10, 7E12, 8A5, 14C9, and 14H3 were found to be only moderately neutralizing (Table 6, lower panel). Unlike the Stx2 Hu-mAbs, the neutralization observed in vitro and in vivo for the Stx1 Hu-mAbs, correlated.

In Vitro Efficacy of Stx1-Specific Hu-mAbs Against Clinical Isolates

An in vitro cytotoxicity assay was utilized to determine the relative efficacy of the Stx1-specific Hu-mAbs, 15G2 and 5A4 against 5 Stx1-producing STEC strains. A neutralization index representing the amount of Stx1 neutralized was determined for each Stx1-specific Hu-mAb-strain combination. Stx1-specific Hu-mAbs, 15G2 and 5A4, were effective at neutralizing the Stx1 produced by each of the 5 clinical isolates tested (FIG. 10). This result is in concordance with the fact that Stx1 is structurally homogeneous.

TABLE 6

Summary of Stx1 Hu-mAb isotype, subunit specificity, and in vivo and in vitro neutralization of Stx1[a].

| mAb | Iso-type[b] | Stx1 Subunit Specificity | HeLa Cell Cytotoxicity Assay (% Neutralization of Stx1 ± S.D.)[c] | Murine Survival[d] Average ± S.D. (days) | p-value |
|---|---|---|---|---|---|
| 2D9 | IgM$_\kappa$ | B | 100.0 ± 0 | 12.0 ± 0[e] | 0.00005 |
| 5A4 | IgG1$_\kappa$ | B | 88.7 ± 1.15 | 12.0 ± 0[f] | 0.00005 |
| 10F4 | IgG1$_\kappa$ | B | 99.7 ± 0.14 | 12.0 ± 0[f] | 0.00005 |
| 15G2 | IgG1$_\kappa$ | B | 96.2 ± 1.59 | 12.0 ± 0[e] | 0.00005 |
| 15G9 | IgM$_\kappa$ | B | 96.9 ± 5.03 | 12.0 ± 0[f] | 0.00005 |
| 1B10 | IgM$_\kappa$ | B | 63.3 ± 18.46 | 9.55 ± 3.95[e] | 0.00071 |
| 7E12 | IgM$_\kappa$ | A | 75.7 ± 9.29 | 9.08 ± 4.52[e] | 0.03389 |
| 8A5 | IgM$_\kappa$ | B | 57.7 ± 10.26 | 5.39 ± 3.77[e] | 0.13821 |
| 13F1 | IgG1$_\kappa$ | B | ND | ND | — |
| 14C9 | IgM$_\kappa$ | B | 76.3 ± 13.35 | 6.80 ± 4.49[e] | 0.14342 |
| 14H3 | IgM$_\kappa$ | B | 77.3 ± 5.91 | 7.95 ± 4.28[e] | 0.00268 |

[a]Stx1 Hu-mAbs have been sorted into two groups based on average percent neutralization of Stx1 in vitro and ability to prolong average in vivo. Upper group includes those Stx1 Hu-mAbs with in vitro percent neutralization values of >85% and average survival prolongation of >10 days. Lower group includes those Stx1 Hu-mAbs with in vitro percent neutralization values of <84% and # average survival prolongation of <10 days. Although not tested in vitro or in vivo, Stx1 Hu-mAb 13F1 is listed in the lower group.
[b]All anti-Stx1 mAbs are comprised of human heavy and light chain isotypes as indicated with the exception of mAb 1E2 which is a hybrid comprised of a murine IgG2a heavy chain and a human kappa light chain.
[c]% Neutralization of 1 ng Stx1 in vitro in presence of 39.1 ng mAb.

TABLE 6-continued

Summary of Stx1 Hu-mAb isotype, subunit specificity, and in vivo and in vitro neutralization of Stx1[a].

| mAb | Iso-type[b] | Stx1 Subunit Specificity | HeLa Cell Cytotoxicity Assay (% Neutralization of Stx1 ± S.D.)[c] | Murine Survival[d] Average ± S.D. (days) | p-value |
|---|---|---|---|---|---|

[d]Experiments were terminated on day 12; n = 6-10. Hu-mAbs which prolonged average survival >10 days are indicated in bold type. p-values were calculated for the comparison of average survival of PBS control groups and Hu-mAb treated groups by parametric (log-rank) and non-parametric (Wilcoxon) analyses. Comparable p-values were obtained with both analyses. The table shows p-values obtained by Wilcoxon analysis.
[e]Average survival of PBS control = 3.45 ± 0.64 days.
[f]Average survival of PBS control = 3.55 ± 0.93 days.

Example 6

Phase I Dose-Escalating Trial to Evaluate the Safety and Pharmacokinetics of 5C12 Human Monoclonal Antibody (Hu-mAb) to Shiga Toxin 2 (Stx2) in Healthy Volunteers A phase I, single site, open label, non-randomized, dose escalation clinical trial of 5C12, a human monoclonal antibody (Hu-MAb) to Shiga toxin 2 (Stx2) in up to 18 volunteers will be conducted. The study will be conducted in healthy volunteers at the General Clinical Research Center (GCRC) at Tufts-New England Medical Center (NEMC). Volunteers will be hospitalized in the Tufts-NEMC GCRC during the infusion and will be discharged after the 24-hour post infusion study procedures have been performed. Three escalating dose cohorts, with six volunteers in each cohort, will be evaluated. No more than one volunteer will be dosed per day (all cohorts). Dose escalation to the next cohort will occur after the safety monitoring committee (SMC) reviews all safety data through Day 7 for all volunteers in the preceding cohort. Division of Microbiology and Infectious Diseases, NIAID, NIH, DHHS will review the SMC's recommendation and will make the final decision as to whether dose escalation to the next cohort can occur. The dose cohorts are 0.1 mg/kg, 0.5 mg/kg, and 5.0 mg/kg of 5C12 (low dose, anticipated therapeutic dose based on animal data and high dose).

A single dose of human monoclonal antibody will be infused intravenously using an infusion pump over at least 2 hours. Volunteers will be evaluated at screening, Day 0, Day 1, Day 2, Day 3, Day 7, Day 14±1, Day 28±3, and Day 56±7. Clinical evaluation for adverse events and laboratory tests will be done at frequent intervals. Safety evaluations (primary outcome) will be assessed using standardized questions during each study visit, standardized physical examinations, and the results of laboratory tests. Volunteers will be reminded during the course of the study to contact the principal investigator for any issues. Volunteers will also be telephoned on Day 5 to solicit adverse events. Pharmacokinetic evaluations (secondary outcome) will also be assessed. Clinical laboratory tests to evaluate safety will be performed at the Clinical Laboratory Improvement Amendments (CLIA)-approved clinical laboratories at Tufts-New England Medical Center. Pharmacokinetic laboratory tests will be performed at Dr. Tzipori's research laboratory at the Cummings School of Veterinary Medicine, Tufts University. All data will be collected using source documents and visit and flow sheets designed for this study. Study specific data will be transcribed onto case report forms.

A safety monitoring committee will oversee the study. This Committee will perform 2 interim analyses—one after all members of the first cohort reach study Day 7 and one after all members of the second cohort reach study Day 7. A formal interim analysis report will be submitted and will contain the following information regarding the study's safety to date:
Summary of safety data evaluation for Days 0-7
Summary of safety data evaluation for the cohort beyond Day 7, if applicable
Summary of safety laboratory test results
Summary assessment
Production of 5C12 Monoclonal Antibody The monoclonal antibody is being produced and the final product will be provided by Biovest International, Inc.

Production Process Development

Initially, a Master Cell Bank vial of Chinese hamster ovary (CHO) 5C12 cells was thawed and expanded into T25 flasks to determine the static antibody production level. These cultures served to verify recovery for the Master Cell Bank and determined the peak antibody level to be 5 µg/mL. Next, split cultures from this static flask study were expanded to create an inoculum for the Acusyst Maximizer hollow fiber bioreactor assessment run.

A Maximizer® containing two hollow fiber bioreactors was inoculated with $0.95 \times 10^8$ viable cells and maintained for 32 days with HyQ® PF CHO™ L/S serum-free medium. The bioreactors reached confluence 15 days later and continued to exhibit glucose consumption and lactate production rates typically observed in healthy, high-density perfusion cultures. After the growth phase (Day 4 to 18), antibody harvest was initiated and 492 mgs of antibody was collected in 2300 mL of supernatant. This equates to an approximate antibody production rate of 19 mg/bioreactor/day. It is expected that these cultures could be maintained for an additional 30 days to essentially double the total quantity of antibody produced.

Purification Process Development

Antibody produced during the Maximizer® assessment was used to develop a purification process that is suitable for early clinical trials.

Approximately 400 mg of antibody (as crude supernatant) was produced during the Maximizer run. The initial purification development processes was performed with 238 mg as a way to preserve additional material for further studies if needed. At present, the following process has been evaluated:
Capture step: Affinity chromatography using Protein A Prosep-vA High Capacity resin (Millipore)
Viral inactivation: Hold eluted antibody at pH 3 for 30 minutes followed by neutralization to pH 7
Dialysis: Buffer exchange into normal saline
DNA removal: Pass neutralized antibody through a Mustang Q (Pall) filter to bind residual DNA
Viral Removal Pass eluate through a Millipore NFP Oticap filter
Concentration and diafiltration: Pass eluate through TFF filter to adjust final product concentration Further development has resulted in approximately 100% recovery after the Protein vA chromatography step. Low pH hold for 30 minutes, did not cause precipitation or loss of antibody. At present, the results indicate that less than 10% of the antibody is lost during the DNA removal step and it is anticipated that further study will slightly improve this rate of recovery. The viral filtration step has been evaluated and there was no product loss observed. The concentration and diafiltration step was limited by the small quantity of starting material, however antibody precipitation at the objective of 5 to 10 mg/mL should not be a problem.

Production

The antibody will be produced in hollow fiber bioreactors. Based on the most recent results available at the time of this submission, 12 grams of 5C12 antibody supernatant will be required to generate 10 grams of purified final product. To do this, two or three Acusyst Xcellerator™ flowpaths will be run for 45-60 days and consume approximately 8,000 liters of media. Any further improvement to the percent recovery during purification will lower the amount of crude supernatant that is needed. Following purification, the bulk final product will be sent to a subcontractor for final fill and finish.

SDS-PAGE

The r5C12 BioVest antibody was run on a reduced SDS-PAGE 4-12% Tris-Bis gel to evaluate purity. As controls, the r5C12 Tufts and 5C12 Hybridoma antibodies, were included on this gel. The amounts loaded for each antibody (2 □g and 4 □g) were based on the concentration used for the in vivo mouse model, HeLa cell cytotoxicity assay and the Stx2-specific Enzyme-Linked Immunosorbent Assay (ELISA). Following electrophoresis, the gel was stained with Coomassie and photographed. Visually, the loadings of the 3 antibodies were equivalent and the antibody bands (heavy and light chains) represented >98% of the total protein. No smears were observed in any of the lanes and the protein profiles of the three antibodies were very similar.

Affinity and Neutralization Data from In Vitro Experiments Using 5C12

The r5C12 BV HuMAb was evaluated for its ability to neutralize the cytotoxic effects of Stx2 against HeLa cells. For comparison, r5C12 produced in CHO cell culture as described in previous examples (referred to as 5C12 Tufts; not purified) was included in this assay. The HuMAbs were assayed from 10 ng to 0.3 ng (two-fold dilutions). The assay was performed as previously described (Akiyosbi, et al., *Infection and Immunity,* 4054-4061 (2005)). Two independent assays were performed, with each antibody concentration tested in triplicate. The r5C12 BioVest and r5C12 Tufts HuMAbs had nearly identical neutralization curves. Fifty percent of the toxin (10 ng) was neutralized by approximately 0.6 ng of either antibody. At 0.3 ng of antibody, the percent neutralization was just over 40%. The data indicate that the r5C12 BioVest has neutralization activity equivalent to the r5C12 produced in CHO cells described in previous examples.

Dosage, Preparation and Administration of 5C12 Monoclonal Antibody

5C12 will be supplied at a concentration of 10 mg/mL in 0.9% normal saline in vials containing 10 mL. The calculated dose of 5C12 assigned to a study volunteer (0.1 mg/kg, 0.5 mg/kg, or 5.0 mg/kg) will be diluted to a total volume of 200 mL in 0.9% NaCl (normal saline) just prior to the infusion. The maximum dose that will be given to a volunteer is 5.0 mg/kg. The vials are single-use. Volunteer allergy information will be double checked just prior to the infusion. The study product solution will be administered intravenously through a sterile 0.22 micron in-line filter using a volumetric pump over at least 2 hours.

Safety evaluations The following evaluations will be performed during the study to assess the safety and tolerability of 5C12. These data will be recorded in source documentation and on the case report form (CRF). A safety analysis will be conducted on all study volunteers who receive a dose of study product.

Vital sign measurements including weight, temperature, resting blood pressure, heart rate and respiratory rate will be taken. The rate of notable vital sign abnormalities will be calculated and summarized by cohort using descriptive statistics. The change from baseline to each post-baseline visit will be summarized by cohort using descriptive statistics.

Physical examination will be performed. The abnormal findings in physical examination will be summarized by treatment group using descriptive statistics.

Clinical laboratory tests (as outlined in Section 8.2) will be performed. Values outside the normal range and clinically significant abnormal range will be flagged in the data listing. Laboratory data will be summarized by treatment group using shift tables (baseline to notable shift post-baseline value). The change from baseline will be summarized by treatment group using descriptive statistics.

Adverse event and reactogenicity assessment Adverse events will be assessed by targeted physical examinations and clinical laboratory testing as described in Section 8. In addition, volunteers will be asked at scheduled clinical visits whether or not they have experienced any adverse events, including, but not limited to, the following symptoms: fever, chills, rash, joint pain or swelling, shortness of breath, headache, fatigue, hives or any other symptoms. Volunteers will be reminded during the course of the study to contact the PI for any issues, including adverse events. Adverse events will also be solicited by a telephone call to the volunteer on Day 5.

All adverse events recorded during the study will be summarized using descriptive statistics. The incidence of treatment-emergent adverse events will be summarized by body system, type of adverse event, intensity (based on DMID grades), and relationship to the investigational product.

The development of human anti-human antibody (HAHA) following the receipt of 5C12 will be measured by a bridging ELISA from blood samples collected pre-infusion (Day 0), on Day 14±1, and on Day 56±10. Samples will be collected in a serum separator tube and stored at −20 to −80° C. The assay will be performed at Dr. Tzipori's laboratory at the Cummings School of Veterinary Medicine, Tufts University.

Pharmacokinetic evaluations Blood samples for the analyses of serum concentrations of Stx2 antibodies will be drawn before and after the completion of study product infusion. Samples will be collected in a serum separator tube. The post infusion samples will be drawn at the end of the infusion, 30 minutes after infusion completion, then at 1 hour, 2 hours, 4 hours, 6 hours, 8 hours and 24±4 hours post infusion. Additional samples will be collected on Days 2, 3, 7, 14±1, 28±3, and 56±17 days. Serum will be aliquoted and stored at −20 to −80° C. The following pharmacokinetic evaluations will be performed: ELISA for binding activity and quantitation of 5C12 in human sera, an in vitro HeLa cell cytotoxicity assay to evaluate the efficacy of 5C12 containing human sera to neutralize the toxic effects of Stx2 exerted against HeLa cells, an ELISA assay to screen samples for human anti-human antibodies (HAHA), and surface HAHA plasmon resonance technology (BIACORE) to evaluate antibody responses against 5C12. All pharmacokinetic evaluations will be performed at Dr. Tzipori's laboratory at the Cummings School of Veterinary Medicine, Tufts University.

Serum concentrations of 5C12 will be determined by a standardized ELISA assay.

The following pharmacokinetic parameters will be estimated and reported:

$T_{1/2}$—Time required to change the amount of drug in the body by one-half during elimination $AUC_{0-t}$—Area under the concentration-time curve from the time of dosing to the time of the last observation (calculated by linear trapezoidal summation)

$AUC_{0-\infty}$—Area under the curve from the time of dosing extrapolated to infinity (calculated by linear trapezoidal summation and extrapolated to infinity)

$C_{max}$—Maximum plasma concentration observed post-dose $T_{max}$—Time at which the Cmax occurs All pharmacokinetic parameters will be summarized using descriptive statistics. Individual as well as mean concentration-time plots will be depicted for $C_{max}$. With regard to AUC, $C_{max}$, and $t_{max}$, an Analysis of Variance (ANOVA) model with dosing cohort as the main factor will be performed to compare groups.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating a human to prevent or ameliorate one or more symptoms of hemolytic uremic syndrome (HUS) comprising administering human or humanized monoclonal antibodies or antibody fragments which only bind specifically to subunit A of the Shiga-like toxin II, in a dosage equal to or greater than 0.4 mg/kg to produce a mean serum concentration of at least 0.7 µg/ml effective to prevent or treat HUS.

2. The method of claim 1 wherein the human monoclonal antibodies which bind specifically to Shiga-like toxin II are neutralizing antibodies.

3. The method of claim 1 wherein the dosage is effective to prevent the human from developing HUS.

4. The method of claim 1 wherein the dosage is administered parenterally.

5. The method of claim 1 wherein the dosage is administered by injection.

6. The method of claim 1 wherein the dosage is administered as a single injection or infusion.

7. The method of claim 1 wherein the dosage is between 0.1 mg/kg-5.0 mg/kg of a neutralizing humanized monoclonal antibody selectively binding the alpha subunit of SLT-II and having a dissociation constant of 0.85 nM.

8. The method of claim 1 wherein a dose of 0.1 mg/kg, 0.5 mg/kg, or 5.0 mg/kg of a neutralizing humanized monoclonal antibody selectively binding the alpha subunit of SLT-II and having a dissociation constant of 0.85 nM is administered.

9. The method of claim 1 wherein the dosage is infused intravenously using an infusion pump over at least 2 hours.

10. The method of claim 1, wherein the antibodies are produced by recombinant DNA methodology.

11. The method of claim 1, wherein the antibodies are chimeric monoclonal antibodies.

12. The method of claim 1 wherein the antibodies are effective to prevent neurological signs of hemolytic uremic syndrome or lesions selected from the group consisting of cerebral hemorrhaging and convulsions.

13. The method of claim 1, wherein the antibodies are effective to prolong survival.

14. The method of claim 1, further comprising administering antibodies binding to the beta subunit of the Shiga-like toxin II.

15. The method of claim 1 in a dosage equivalent to 4 ml serum from an animal immunized with Shiga-like toxin II/kg body weight.

16. The method of claim 1 in a dosage producing a serum level of anti-Shiga toxin II antibodies of at least 0.5 micrograms/ml.

17. The method of claim 1 in a dosage of 3 mg human monoclonal antibody to Shiga-like toxin II administered to a newborn pig.

* * * * *

UNITED STATES PATENT AND TRADEMARK OFFICE
CERTIFICATE OF CORRECTION

| | | |
|---|---|---|
| PATENT NO. | : 7,910,096 B2 | |
| APPLICATION NO. | : 11/933166 | |
| DATED | : March 22, 2011 | |
| INVENTOR(S) | : Saul Tzipori and Arthur Donohue-Rolfe | |

It is certified that error appears in the above-identified patent and that said Letters Patent is hereby corrected as shown below:

Column 1, Lines 15-18, replace
"The federal government may have certain rights in the invention since funding for the work described herein was provided in part by the NIH grants R01-AI41326 and R01-DK58993."
with
--This invention was made with government support under grants R01-AI41326 and R01-DK58993, awarded by the National Institutes of Health. The government has certain rights in the invention.--

Signed and Sealed this
Twenty-third Day of October, 2012

David J. Kappos
*Director of the United States Patent and Trademark Office*